US012238256B1

(12) United States Patent
James, Jr.

(10) Patent No.: US 12,238,256 B1
(45) Date of Patent: Feb. 25, 2025

(54) SYSTEM AND METHOD FOR MAPPING COLORS OF A COLOR CALIBRATED IMAGE OR VIDEO

(71) Applicant: TRUE-See Systems, LLC, New Orleans, LA (US)

(72) Inventor: Francis Godwin James, Jr., New Orleans, LA (US)

(*) Notice: Subject to any disclaimer, the term of this patent is extended or adjusted under 35 U.S.C. 154(b) by 248 days.

(21) Appl. No.: 18/084,137

(22) Filed: Dec. 19, 2022

Related U.S. Application Data

(63) Continuation-in-part of application No. 17/185,939, filed on Feb. 25, 2021, now Pat. No. 11,961,260, (Continued)

(51) Int. Cl.
| | |
|---|---|
| *G06T 7/00* | (2017.01) |
| *G06K 7/14* | (2006.01) |
| *G06T 1/00* | (2006.01) |
| *G06T 7/62* | (2017.01) |
| *G06T 7/80* | (2017.01) |
| *G06T 7/90* | (2017.01) |
| *G06T 17/00* | (2006.01) |
| *G06T 19/20* | (2011.01) |
| *G06V 10/56* | (2022.01) |
| *G06V 10/74* | (2022.01) |
| *G16H 10/60* | (2018.01) |
| *G16H 30/20* | (2018.01) |
| *H04N 1/60* | (2006.01) |
| *H04N 9/64* | (2023.01) |
| *H04N 23/67* | (2023.01) |

(52) U.S. Cl.
CPC ............. *H04N 1/60* (2013.01); *G06T 1/0021* (2013.01); *G06T 7/62* (2017.01); *G06T 7/90* (2017.01); *G06V 10/56* (2022.01); *G06V 10/761* (2022.01); *H04N 23/67* (2023.01); *G06T 2207/10024* (2013.01)

(58) Field of Classification Search
CPC ......... G06T 7/90; G06T 7/0016; G06T 17/00; G06T 19/20; G06T 2200/04; G06T 2207/10028; G06T 2210/41; G16H 10/60; G16H 30/20; A61B 5/0077; A61B 2576/00; A61B 5/0059–0075; A61B 90/90–96
See application file for complete search history.

(56) References Cited

U.S. PATENT DOCUMENTS

| | | | | |
|---|---|---|---|---|
| 5,027,587 A | * | 7/1991 | Ramsey | B43M 3/04 53/493 |
| 5,760,913 A | * | 6/1998 | Falk | H04N 1/6033 358/518 |

(Continued)

*Primary Examiner* — Oommen Jacob
(74) *Attorney, Agent, or Firm* — AdamsIP, LLC; Stephen Thompson; J. Hunter Adams

(57) ABSTRACT

A system and method for mapping colors of a color calibrated image or video are provided. An image or video may first be color calibrated. The colors appearing in different areas of the image or video may then be compared to one or more selected target colors to determine if color values of the colors appearing in the image or video are within a selected color value tolerance of the target color. If areas of the image or video are within the tolerance, those areas may be visually delineated from other areas to display one or more mapped color areas within the image or video.

20 Claims, 25 Drawing Sheets

Related U.S. Application Data which is a continuation-in-part of application No. 14/209,557, filed on Mar. 13, 2014, now Pat. No. 10,973,412.

(60) Provisional application No. 61/799,843, filed on Mar. 15, 2013.

(56) References Cited

U.S. PATENT DOCUMENTS

| | | | | |
|---|---|---|---|---|
| 5,799,105 | A * | 8/1998 | Tao | B07C 5/3422 348/30 |
| 5,836,872 | A * | 11/1998 | Kenet | G06T 7/0012 382/128 |
| 6,062,137 | A * | 5/2000 | Guo | H04N 1/52 400/70 |
| 6,178,007 | B1 * | 1/2001 | Harrington | H04N 1/6036 358/1.9 |
| 6,603,574 | B1 * | 8/2003 | Ramirez | H04N 1/00031 399/41 |
| 6,993,167 | B1 * | 1/2006 | Skladnev | A61B 5/0059 382/128 |
| 7,050,196 | B1 * | 5/2006 | Piatt | H04N 1/4078 358/1.9 |
| 8,123,704 | B2 * | 2/2012 | Richards | A61B 5/107 600/587 |
| 8,259,369 | B2 * | 9/2012 | Klassen | H04N 1/6033 358/518 |
| 8,823,934 | B2 * | 9/2014 | Chhibber | H04N 13/254 382/165 |
| 8,848,988 | B2 * | 9/2014 | Plickert | G01N 21/8483 382/128 |
| 8,849,380 | B2 * | 9/2014 | Patwardhan | A61B 5/442 600/317 |
| 10,973,412 | B1 * | 4/2021 | James, Jr. | A61B 5/1034 |
| 2002/0123671 | A1 * | 9/2002 | Haaland | A61B 5/0002 600/300 |
| 2002/0140990 | A1 * | 10/2002 | Liu | H04N 1/00053 358/406 |
| 2003/0004946 | A1 * | 1/2003 | VanDenAvond | G06Q 10/10 707/999.009 |
| 2003/0007191 | A1 * | 1/2003 | Herbert | G06F 3/14 358/1.9 |
| 2003/0055341 | A1 * | 3/2003 | Banerjee | G01N 33/533 600/476 |
| 2003/0216836 | A1 * | 11/2003 | Treat | A61B 90/92 700/245 |
| 2003/0217662 | A1 * | 11/2003 | Koifman | B41C 1/1075 101/484 |
| 2003/0225324 | A1 * | 12/2003 | Anderson | A61B 5/412 600/364 |
| 2004/0000246 | A1 * | 1/2004 | Keane | G06F 3/1205 101/483 |
| 2004/0078299 | A1 * | 4/2004 | Down-Logan | G06Q 30/02 705/26.1 |
| 2004/0163562 | A1 * | 8/2004 | Lewis, Jr. | B41F 33/0081 101/485 |
| 2005/0093923 | A1 * | 5/2005 | Busch | H04N 1/6033 347/43 |
| 2005/0261551 | A1 * | 11/2005 | Couvillon, Jr. | A61B 1/00059 600/109 |
| 2007/0242877 | A1 * | 10/2007 | Peters | G06V 10/75 382/167 |
| 2007/0287191 | A1 * | 12/2007 | Stiene | A61B 5/1486 427/209 |
| 2008/0175430 | A1 * | 7/2008 | Fan | H04N 1/32144 382/100 |
| 2009/0317002 | A1 * | 12/2009 | Dein | A61B 50/20 340/568.1 |
| 2010/0121201 | A1 * | 5/2010 | Papaioannou | A61B 5/0064 382/128 |
| 2010/0195902 | A1 * | 8/2010 | Horovitz | H04N 1/603 382/162 |
| 2011/0117025 | A1 * | 5/2011 | Dacosta | A61B 5/0059 435/5 |
| 2011/0293153 | A1 * | 12/2011 | Plickert | G01N 21/8483 382/128 |
| 2012/0253122 | A1 * | 10/2012 | Minetoma | A61B 1/000094 600/109 |
| 2015/0288952 | A1 * | 10/2015 | Popilka | A61B 5/4547 348/46 |
| 2017/0082493 | A1 * | 3/2017 | Nagai | G06T 11/206 |
| 2018/0181793 | A1 * | 6/2018 | Ariga | H04N 1/6033 |

* cited by examiner

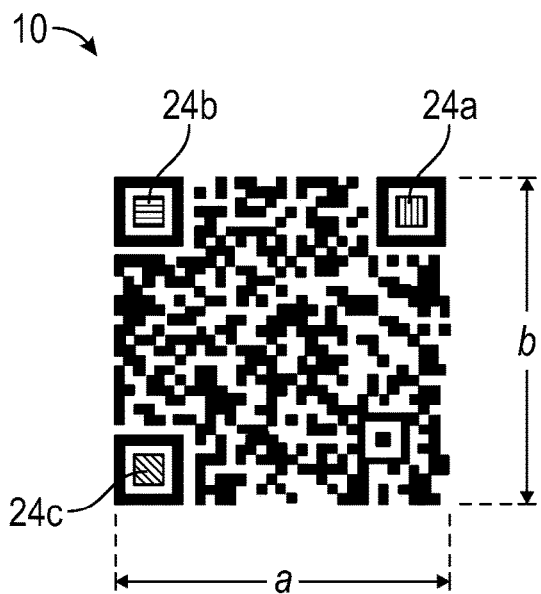
FIG. 3
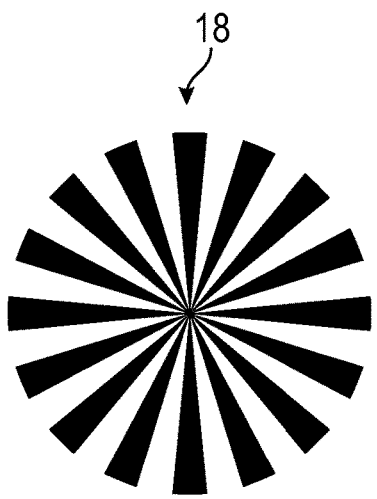
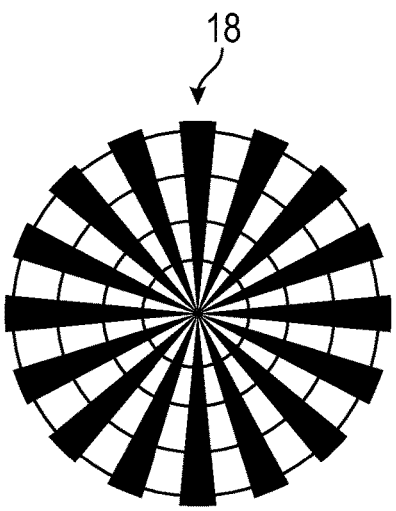
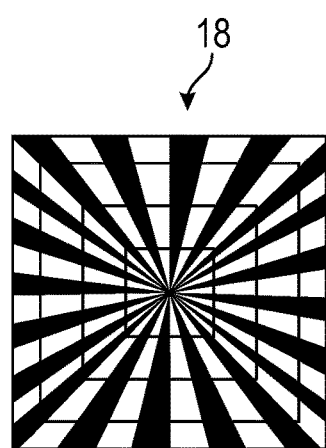
FIG. 4A　　　　　　FIG. 4B　　　　　　FIG. 4C 2D Color and Segmentation Analysis 3D Color and Segmentation Analysis

SYSTEM AND METHOD FOR MAPPING COLORS OF A COLOR CALIBRATED IMAGE OR VIDEO

CROSS REFERENCES

This application is a continuation-in-part of U.S. application Ser. No. 17/185,939, filed on Feb. 25, 2021, which is a continuation-in-part of U.S. application Ser. No. 14/209,557, filed on Mar. 13, 2014, now U.S. Pat. No. 10,973,412, issued Apr. 13, 2021, which claims the benefit of U.S. Provisional Application No. 61/799,843, filed on Mar. 15, 2013, which applications are incorporated herein by reference in their entirety.

FIELD OF THE DISCLOSURE

The subject matter of the present disclosure refers generally to a system and method for mapping colors of a color calibrated image or video.

BACKGROUND

Photo-documentation is widely used in the medical field to create a visual record of patient wounds and skin conditions. Medical photo-documentation is a critical aspect of the medical record for wounds and skin conditions because such documentation provides a visual component to the medical record to support a written diagnosis and course of care. Thus, in medical photo-documentation, the accuracy of the color of visual representations is important as such representations may be critical to diagnosis and treatment of wounds or skin conditions, as well for assessment of the efficacy of a rendered course of treatment and for medical reimbursement purposes. Medical photo-documentation may include both still images and videos of patient subjects. However, the color consistency and accuracy of color photographs and videos used in the medical field may vary significantly due to a variety of factors, such as the type of device used to capture a specific photograph or video, the lighting that illuminates the subject of the photograph or video, and differences in camera and video settings, among other factors. In addition, most, if not all, current visual recording devices utilize software to adjust and manipulate the color of an image or video without reference to a known color or photographic standard by which to judge the accuracy of the color of the photograph or video. Further, the colors of captured still or moving images may be automatically manipulated by camera software without any means of verifying that color manipulation has or has not occurred. These factors may cause the visual medical record of a patient to be not only inaccurate but also unverifiable. If any of these factors cause the medical record to inaccurately represent the medical subject, diagnosis and/or evaluation of the patient may be adversely affected.

In addition to accurate color representation, diagnosis and/or evaluation of a patient, particularly of patient wounds, also requires an accurate depiction of the depth of a wound and how the depth or contours of the wound change over time during the healing process. Different portions of wounds, particularly severe wounds covering substantial portions of the patient's body, may heal at different rates, during which time the depth of the wound may change. Thus, to provide a full indication of the condition of a wound at any given time, medical professionals must have an accurate depiction of both the color of all parts of the wound as well as the depth and contours of the wound. The color of different portions of a wound may provide medical professionals with important information regarding the present status or progress of a wound as it heals. In addition, it is important for medical professionals to understand how the depth of a wound has changed to fully evaluate the healing process. However, typical photo-documentation of patient wounds does not generally provide an accurate representation of the contours of wounds and how those contours change during the healing process, thereby providing an incomplete picture to medical professionals of how patient wounds develop.

In addition, video representations may be utilized for both video documentation of wounds or other skin conditions or for analyzing motion of a subject, such as in the case of a subject's movement during physical therapy or rehabilitation. Video documentation may be utilized to evaluate physical or neurological disorders by analyzing motion of the subject due to symptoms or conditions of a patient, such as changes in gate or balance of the subject when walking or performing other motions, or by analyzing involuntary motion such as motions that occur during tremors or seizures. In other applications, video documentation may be used to record operations or other types of surgical procedures. In such applications, video may be used to capture motion of the subject, motion of the capturing device in relationship to the subject, or simultaneous motion of both the subject and device.

Accordingly, a need exists in the art for a system and method of providing an accurate visual representation of a wound or skin condition of a patient, whether through still images or video, including both the color and the contours of the wound or skin condition.

Furthermore, a need exists in the art for a system and method of providing a consistently accurate visual representation, whether through still images or video, including both color and contour, of how a patient wound or skin condition changes over a period of time.

In addition, a need exists in the art for color calibrated and uniquely identified image sequences that can be verified as unaltered for reliability and security to protect the integrity of the medical record so that the image sequences and individual images in the sequences can be relied upon for medical analysis of motion and/or color.

Furthermore, a need exists in the art for a system and method of certifying image sequences and individual images in the sequences as unaltered for reliability and security to protect the integrity of the medical record.

In addition, a need exists in the art for a system and method for visually delineating areas of generally different colors from each other within an image or video for color evaluation of the image or video.

SUMMARY

A system and method of producing medical image data that provides consistently accurate visual representations of medical images and videos are provided. The images or videos may be two-dimensional or three-dimensional and may be used for documenting patient wounds or skin conditions, patient movement, or other visual aspects of patient care. The images or videos may be certified as being color calibrated and as being unaltered to protect the integrity of the medical record.

In one aspect, a method of color calibrating a three-dimensional still image or video related to the medical field is provided. In one embodiment, the method comprises capturing one or more two-dimensional images of a subject on an image recording device and then producing a color calibrated three-dimensional image of the same subject. Each two-dimensional image, as well as the three-dimensional image, includes a calibration slate appearing in the image, which in each image is the same calibration slate. The calibration slate is positioned adjacent to the subject and may be attached directly to the subject of the images, and may preferably include an adhesive strip on the back of the calibration slate for attaching the slate to the subject. The calibration slate includes a print run number that identifies a batch of printed calibration slates, which includes the calibration slate appearing in the image. The calibration slate also includes a unique identifier that individually identifies the particular calibration slate appearing in the image. The calibration slate has a color chart comprising at least one color, and preferably a set of colors, for color calibrating each image.

In a preferred embodiment, to produce the three-dimensional image of the subject, the method includes generating point cloud data relating to the subject of each of the two-dimensional images. A three-dimensional model of the subject may then be constructed utilizing the point cloud data. One or more two-dimensional images may then be applied to the three-dimensional model to produce the three-dimensional image of the subject, which also shows the calibration slate that appears in each two-dimensional image. Alternatively, other suitable methods of producing a three-dimensional image may be utilized. For instance, the three-dimensional image may be constructed utilizing a plurality of two-dimensional images of the subject, which may be captured from varying angles relative to the subject, each including the same calibration slate in the image. To correct skew when capturing two-dimensional images of the subject from varying angles, the scale of objects relating to the subject and appearing in each of the two-dimensional images may be determined based on known measurements of one or more objects printed on the calibration slate that appears in each of the two-dimensional images.

To color calibrate the three-dimensional image, the system may measure numeric color values from one or more colors in the color chart printed on the calibration slate that appears in each image to be calibrated. Thus, because the calibration slate appears within the image, color values are measured from the captured image itself when measuring the color values from the calibration slate. The system may then read the print run number on the calibration slate and associate the print run number with a batch of printed calibration slates that includes the specific calibration slate appearing in the image. Because each calibration slate in the batch, including the slate appearing in the image, is substantially similar, the measured numeric color values have corresponding known numeric color values associated with the batch of calibration slates. The measured numeric color values may then be compared to the corresponding known numeric color values. Based on this comparison, the system may calculate a variance between the numeric color values measured from the image to be calibrated and the corresponding known numeric color values. The system may then calculate a calibration factor based on the variance. Once a calibration factor has been determined, the three-dimensional image may be color calibrated based on the calibration factor. In a preferred embodiment, to calibrate the three-dimensional image, each two-dimensional image is individually calibrated by adjusting the colors of each respective two-dimensional image by applying the calibration factor to numeric color values measured from each of the two-dimensional images. Alternatively, the three-dimensional image may be calibrated directly by adjusting the colors of the three-dimensional image by applying the calibration factor to numeric color values measured from the three-dimensional image itself. In addition, the system may read the unique identifier and validate the specific calibration slate used based on the unique identifier to verify that the calibration slate has not been previously used, which prevents potential cross-contamination between patients. The unique identifier is preferably in the form of a machine-readable bar code.

Once the calibration of the three-dimensional image is complete, the user will have a visual representation that accurately shows the colors of the patient wound regardless of any external factors that may affect the visual appearance of the wound, thereby giving medical professionals necessary information for accurately diagnosing and evaluating the patient. In addition, the user may manipulate the three-dimensional image to view an accurate visual representation of the contours of the wound in three dimensions. The system may also be used to measure the physical parameters, including depth, of the wound and to monitor how the wound changes over a period of time, including both the color of the wound and the depth or other parameters of the wound. Thus, the present system provides a complete and accurate visual representation of wounds or skin conditions for medical professionals and provides the ability to monitor how these characteristics change with time.

In another aspect, a method of color calibrating a video is provided. The method comprises capturing a video of a subject on a recording device with a calibration slate appearing in at least one frame of a sequence of frames of the video. A numeric color value may then be measured from a color of the color chart on the calibration slate. The measured numeric color value may then be compared to the corresponding known numeric color value associated with the batch of slates that includes the calibration slate appearing in the frame. The variance between these color values may then be used to calculate a calibration factor, which may be applied to numeric color values measured from the frame in which the calibration slate appears to adjust the colors of the frame to produce a color calibrated frame. In one embodiment, the same calibration factor may be applied to colors of each one of the frames, including frames in which the calibration slate may not appear, to produce a color calibrated video. In another embodiment, the method may comprise a dynamic calibration method in which one or more frames are color calibrated utilizing the calibration slate and then additional frames are calibrated utilizing already-calibrated frames. In this embodiment, color values measured from frames that have not yet been calibrated may be compared to color values from a calibrated frame to calculate a variance and calibration factor, which may then be used to calibrate one or more additional frames. The calibration slate does not need to appear in every frame and may appear in only a single frame.

In another aspect, a method of segmenting and mapping colors of still images or videos is provided. The still images or videos may be two-dimensional or three-dimensional. The method comprises first color calibrating an image, which may be a still image or a frame of a video, utilizing a calibration slate appearing in the still image or at least one frame of the video. Once the image has been calibrated, a target color having a known numeric color value is selected. The target color may be selected based on a particular application. For instance, when calibrating an image of a wound, a red, yellow, black, or white target color may be selected as these colors are often present in wounds and represent different types of tissues commonly observed in wounds. Next, a color value tolerance relating to the known numeric color value associated with the target color is selected. For instance, a desired tolerance of 10% from a selected red target color having known numeric color values may be selected. The desired tolerance may be selected based on the particular application and selected target color. A numeric color value may then be measured from one or more calibrated colors of the color calibrated image and compared to the known numeric color value associated with the target color to determine whether the measured numeric color value is within the selected color value tolerance of the known numeric color value. The measured color values may be measured from discrete image units, such as one or more pixels, of the color calibrated image. The image units with colors that are within the color value tolerance may be delineated from other areas with colors that are not within the tolerance to produce a mapped area that is visually displayed on the color calibrated image. Multiple target colors may be selected to segment multiple colors from each other and produce mapped areas of multiple colors displayed on the image. For instance, if a wound includes some areas that are generally red in color within a selected tolerance of a red target color and some areas that are generally yellow within a selected tolerance of a yellow target color, then different portions of the wound may be segmented and mapped as separate red and yellow areas. The calibration slate may also be utilized to determine size measurements of the mapped areas. Thus, the method may be utilized to evaluate the condition of a wound and to determine how areas of a wound of different colors have changed.

The foregoing summary has outlined some features of the system and method of the present disclosure so that those skilled in the pertinent art may better understand the detailed description that follows. Additional features that form the subject of the claims will be described hereinafter. Those skilled in the pertinent art should appreciate that they can readily utilize these features for designing or modifying other structures for carrying out the same purpose of the system and method disclosed herein. Those skilled in the pertinent art should also realize that such equivalent designs or modifications do not depart from the scope of the system and method of the present disclosure.

DESCRIPTION OF THE DRAWINGS

These and other features, aspects, and advantages of the present disclosure will become better understood with regard to the following description, appended claims, and accompanying drawings where:

FIG. 3 shows an alternative embodiment of a calibration slate that may be utilized for calibrating three-dimensional images in accordance with the present disclosure.

FIG. 4A shows a focus chart that may be printed on a calibration slate that may be utilized for calibrating three-dimensional images in accordance with the present disclosure.

FIG. 4B shows a focus chart that may be printed on a calibration slate that may be utilized for calibrating three-dimensional images in accordance with the present disclosure.

FIG. 4C shows a focus chart that may be printed on a calibration slate that may be utilized for calibrating three-dimensional images in accordance with the present disclosure.

DETAILED DESCRIPTION

In the Summary above and in this Detailed Description, and the claims below, and in the accompanying drawings, reference is made to particular features, including method steps, of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with/or in the context of other particular aspects of the embodiments of the invention, and in the invention generally.

The term "comprises" and grammatical equivalents thereof are used herein to mean that other components, steps, etc. are optionally present. For example, a system "comprising" components A, B, and C can contain only components A, B, and C, or can contain not only components A, B, and C, but also one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

Figure 1:
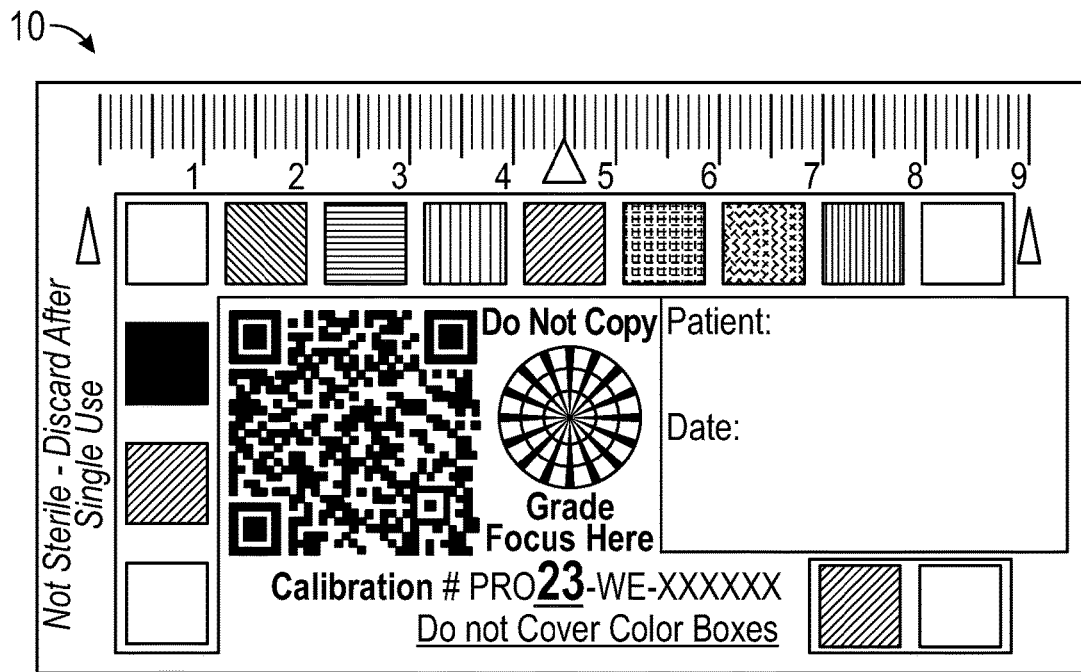
FIG. 1 shows a calibration slate that may be utilized for calibrating three-dimensional images in accordance with the present disclosure.
Figure 2:
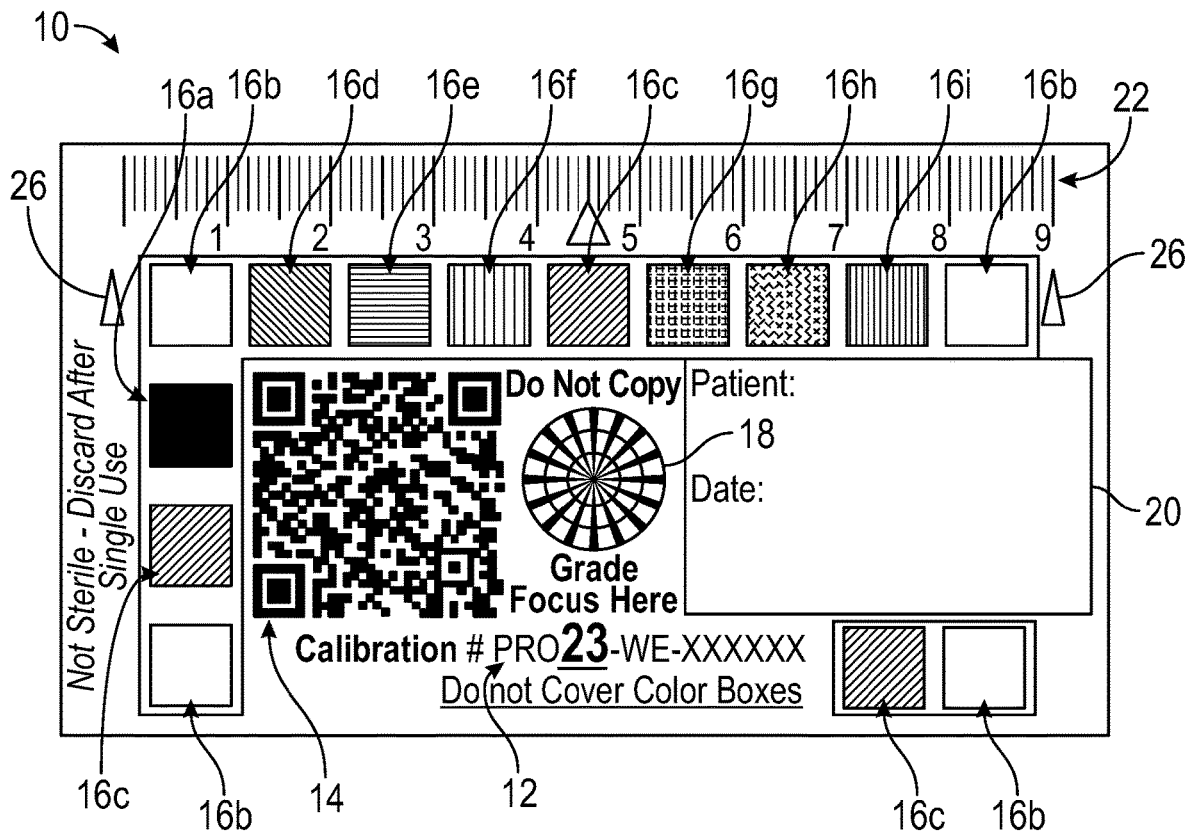
FIG. 2 shows a calibration slate that may be utilized for calibrating three-dimensional images in accordance with the present disclosure.
Figure 14:
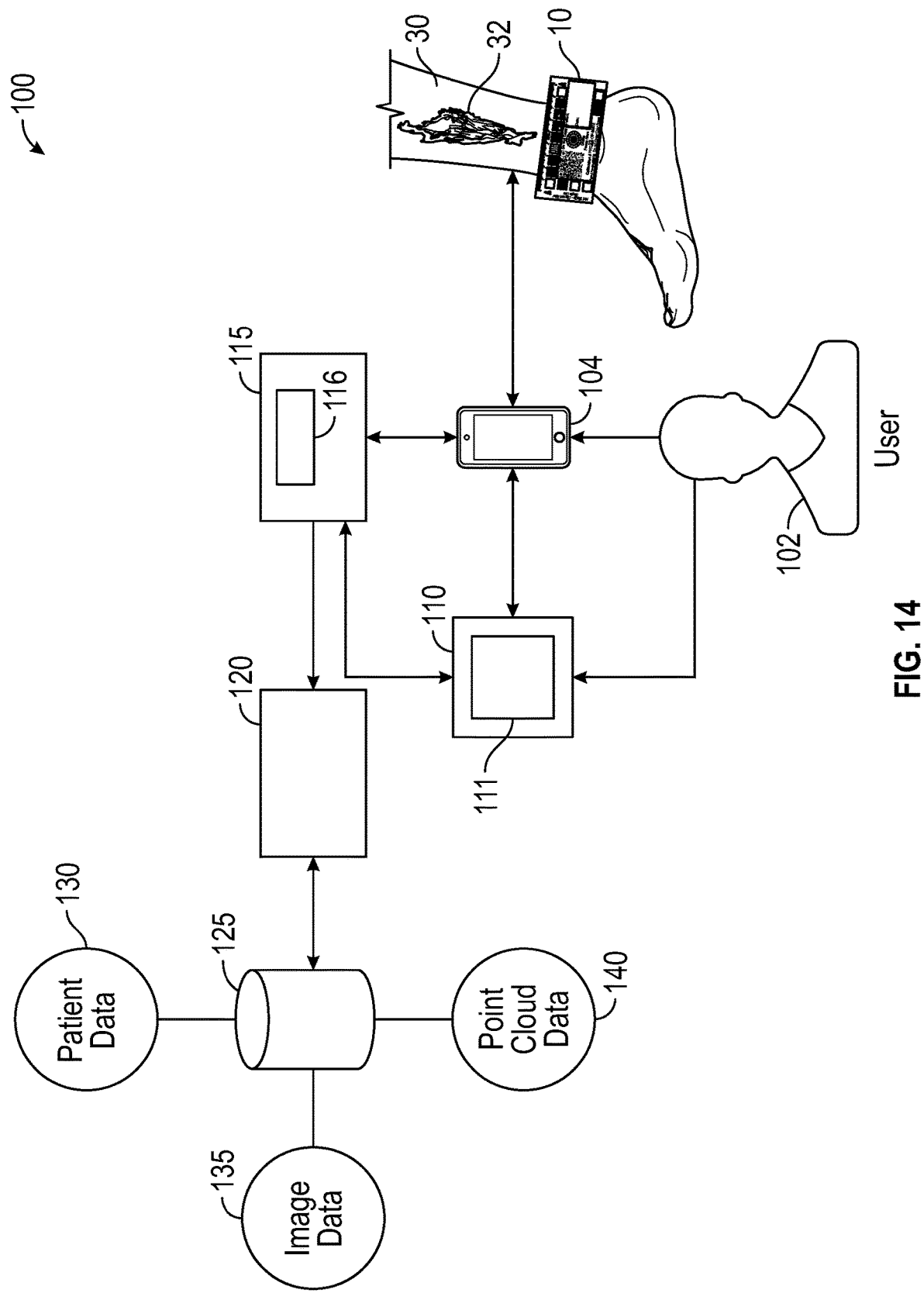
FIG. 14 shows a system for producing color calibrated images or videos using a calibration slate in accordance with the present disclosure.

A system and method of producing medical image data that provides consistently accurate visual representations of medical images or videos are provided. The images or videos may be two-dimensional or three-dimensional and may be certified as being color calibrated and as being unaltered to protect the integrity of the medical record. FIG. 14 illustrates an example system 100 that may be utilized to carry out the present method of producing color calibrated two-dimensional or three-dimensional medical images and videos using a calibration slate 10. FIG. 1 illustrates an illustrative calibration slate 10 that may be utilized in accordance with the present system 100 and method to color calibrate an image or video relating to the medical field, such as a wound or a skin condition. As used herein, the term "medical field" refers generally to any field of medicine and may include wound care, dermatology, forensic medicine, veterinary medicine, or other related medical fields, and may also include any field related treatment, evaluation, testing, or study in the medical field, which may also include the analysis and evaluation of physical or neurological conditions or disorders, particularly through the evaluation of physical movements of a patient, which may be voluntary or involuntary movements, including in home health settings in which a medical professional evaluates a patient's movements through remote observation. In addition, videos related to the medical field may also include videos of fitness activities, tasks performed by the subject, or any other activity as evidence of its occurrence and for analysis. FIG. 2 illustrates a calibration slate 10 with particular features of the slate identified. The calibration slate 10 includes certain features that may be utilized to calibrate an image or video and to validate the slate, including a print run number 12, a unique identifier 14, and a color chart 16. The color chart 16 is printed on each slate 10 and comprises at least one color and preferably a set of colors 16a-16i for color calibrating each captured image 42 or video 242, which includes a calibration slate 10 appearing within the image or video with the color chart 16 visible in the image or video. The print run number 12 identifies a batch of printed calibration slates 10 comprising a plurality of separate individual slates that are all printed as part of one batch, or print run. Thus, the print run number 12 printed on a slate 10 appearing in a captured image 42 or video 242 identifies a specific batch of slates that includes the calibration slate 10 appearing in each image or video to be calibrated. Because the slates in a batch are all printed as a group in one print run, each calibration slate 10 in the batch of printed slates is substantially similar to all slates within the batch, including the color values of all colors of the color chart 16 printed on each slate 10. Because all slates within a batch are substantially similar, associating a particular slate 10 appearing within an image 42 or video 242 with a batch of slates provides a standard for comparing measured color values from the image 42 or video 242 to be calibrated to the standard, which has known numeric color values, thereby facilitating accurate color calibration of the image 42 or video 242 showing the calibration slate 10 in the captured image or video. As used herein, the term "captured image" or "captured video" or grammatical equivalents thereof refer to an image or video captured as is by a recording device 104 capable of capturing still images and/or videos, such as a camera or video recorder, that has not yet been subsequently altered or manipulated by the present system 100.

In a preferred embodiment, the color chart 16 is in the form of a color matrix comprising a plurality of individual discrete boxes each printed a respective color and having a defined border and known dimensions. FIG. 1 illustrates one illustrative arrangement of the color matrix, though it should be understood that other arrangements are possible and would fall within the scope of the present disclosure. As best seen in FIG. 2, in a preferred embodiment, the color chart 16 printed on each calibration slate 10 includes respective, discrete boxes printed in the colors of black 16a, white 16b, grey 16c, green 16d, cyan 16e, magenta 16f, yellow 16g, orange 16h, and red 16i, though it should be understood that other colors may be utilized in addition to or in place of one or more of these colors and still fall within the scope of the present disclosure. One or more, and any combination of colors 16, may be utilized for color calibrating a two-dimensional or a three-dimensional image or video.

In a preferred embodiment, the calibration slate 10 also includes a unique identifier 14 that individually identifies the particular calibration slate 10 appearing in the image 42 or video 242 to be calibrated. As shown in FIG. 2, the unique identifier is preferably in the form of a machine-readable bar code 14, which is preferably a Quick Response (QR) code. The calibration slate 10 may be validated based on the unique identifier 14, preferably by the system 100 reading the bar code 14. By validating the calibration slate 10, the system 100 verifies the source of the slate and that the specific calibration slate shown in the image or video to be calibrated has not been previously used for calibration, thereby preventing potential cross contamination between patients due to the calibration slate coming into physical contact with the patient when capturing the image or video. Each calibration slate 10 is positioned adjacent to the subject and preferably includes an adhesive strip on the back of the calibration slate for directly attaching the slate to the subject, which is the patient. The calibration slates are typically not sterilized and should thus be discarded after a single use.

In a preferred embodiment, as shown in FIG. 2, each calibration slate 10 may include a unique identifier 14 that is separate from the print run number 12. In alternative embodiments, the unique identifier 14, which is unique to each individual respective calibration slate 10, and the print run number 12, which is not unique to individual slates but is unique only to a batch comprising a plurality of individual slates all having the same print run number 12, may both be embodied within a single identifier. For instance, the bar code 14 printed on a calibration slate 10 may be unique to that individual slate, but may also include information relating to the batch of slates from which that individual slate originates. In another alternative embodiment, the print run number 12 may include a plurality of individual numeric digits, letters, or other characters, which may include the print run number identifying the batch from which that individual slate originates, as well as a series of additional characters that are unique to that individual slate 10 for the purpose of identifying only that individual slate. Thus, the print run number 12 on the calibration slate may include a series of characters that collectively provide both the print run number and the unique identifier. Although a preferred embodiment, as shown in FIG. 2, shows the print run number 12 and unique identifier 14 as separate, discrete printed elements on the calibration slate 10, it should be understood by one skilled in the art that any calibration slate having a identifying markings of any type that may be used to uniquely identify that individual slate, as well as to identify the batch of printed slates from which that individual slate originates, would be considered to include both a print run number 12 and a unique identifier 14 as these terms are used herein and would fall within the scope of the present disclosure.

FIG. 3 illustrates an alternative embodiment in which the calibration slate 10 includes only a unique bar code and a color matrix. The unique bar code identifies the individual slate and also includes information that identifies the batch of printed slates from which the slate originates. The bar code preferably has a generally rectangular shape having known dimensions (a and b) that may be used as a measurement scale when capturing an image or video to be calibrated. In this embodiment, the color matrix 24 comprises a minimum number of colors, which preferably include red 24*a*, blue 24*b*, and green 24*c*. The colors are preferably contained within boxes positioned at corners of the bar code.

In a preferred embodiment, as shown in FIG. 2, the calibration slate 10 includes a focus chart 18 comprising concentrically arranged shapes. The focus chart 18 is configured such that it can be used for grading the focus of images or videos to be calibrated. When capturing an image or video, the focus chart may be utilized to aid in focusing the image or video to provide better images for the visual medical record. FIGS. 4A, 4B, and 4C show alternative embodiments of focus charts 18 that may be utilized on the calibration slate 10. The concentrically arranged shapes of the focus chart allow the system 100 to detect multiple levels of focus accuracy by determining how many levels inside the concentric shapes for which the system can detect fidelity and detail. Alternatively, the QR code 14 or a similar feature printed on the slate may be utilized for focusing an image. For instance, the system may read the QR code and determine whether a threshold of focus is achieved in that part of the image to be captured. This feature of the calibration slate provides focus grading that helps to determine if the focus fidelity of the image is acceptable, thereby saving time by rejecting poor, unacceptable image quality, which would result in poor or erroneous visual medical records that would not adequately serve the purpose of accurately representing the patient or subject.

In a preferred embodiment, as shown in FIG. 2, the calibration slate 10 includes a ruler 22 with measurement markers at a top end of the slate for visually measuring the dimensions of a wound 32 or other skin feature when the slate is attached to the subject 30 adjacent to the wound. The slate 10 preferably also includes arrows 26 printed on the slate and pointing upward toward the top of the slate to indicate the proper orientation of the slate when positioning the slate 10 adjacent to the subject 30 of the image or video. Preferably, the calibration slate 10 also includes a blank box 20 in which a medical professional may manually write notes relating to the patient who is the subject 30 of the medical image or video and to whom the slate 10 will be associated. This space 20 may preferably include patient identification information, such as the patient's name or other identifying information, as well as the date that the specific calibration slate 10 is used for the patient. This information may be used to associate a specific calibration slate with a particular patient. In a preferred embodiment, patient identification information may be machine-readable. Preferably, the system 100 allows a medical professional to link a calibration slate 10 to a particular patient using the bar code 14. Thus, the bar code 14 on a specific slate 10 may be scanned and linked to a particular patient including all of the patient identification information associated with the patient.

In one aspect, a method of color calibrating a three-dimensional image 48 or video is provided. In this embodiment, the method generally comprises capturing one or more two-dimensional images 42 of a subject 30 on an image recording device 104 and then producing a color calibrated three-dimensional image 48 of the same subject 30 based on the one or more two-dimensional images 42. As used herein, a "three-dimensional" image refers to a three-dimensional construct, which may include three-dimensional image data, such as point cloud data, in addition to a visual skin imposed upon the three-dimensional construct to produce the image. FIG. 14 illustrates a system 100 that may be used to produce and calibrate the three-dimensional image 48. Each two-dimensional image, as well as the three-dimensional image, includes a calibration slate 10 appearing within the image.

The same calibration slate 10 appears in all of the images for a single iteration of the process. Consecutive iterations of the process may be carried out at spaced time intervals, which allows both qualitative and quantitative analysis of how the wound 32 changes with time during the healing process. The process provides a complete and accurate visual representation of both the color of the wound 32 and the depth and general contours of the wound in order to allow medical professionals the ability to monitor how colors and contours of the wound change with time. Providing an accurate visual representation of both the color and contours of a wound in a three-dimensional representation gives medical professionals a complete picture of a wound as wounds generally change both in color and in depth during the healing process. Thus, accurate wound color and contour information provides medical professionals with all necessary information to provide optimal medical treatment to patients.

Figure 7:
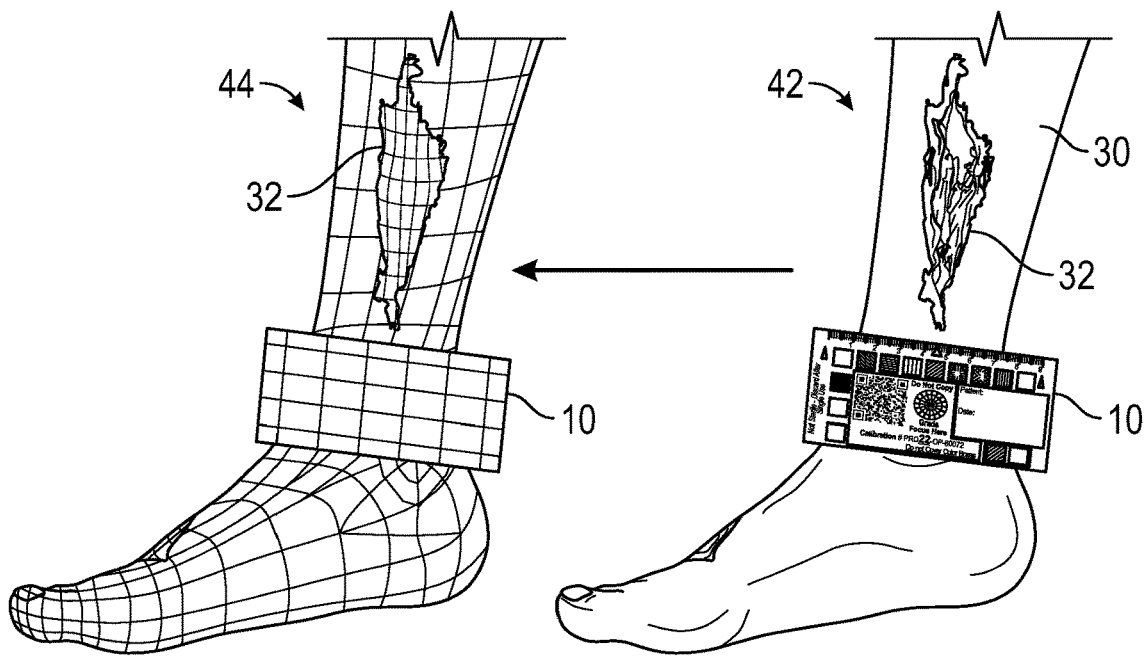
FIG. 7 shows a three-dimensional model of a subject in accordance with the present disclosure.
Figure 8:
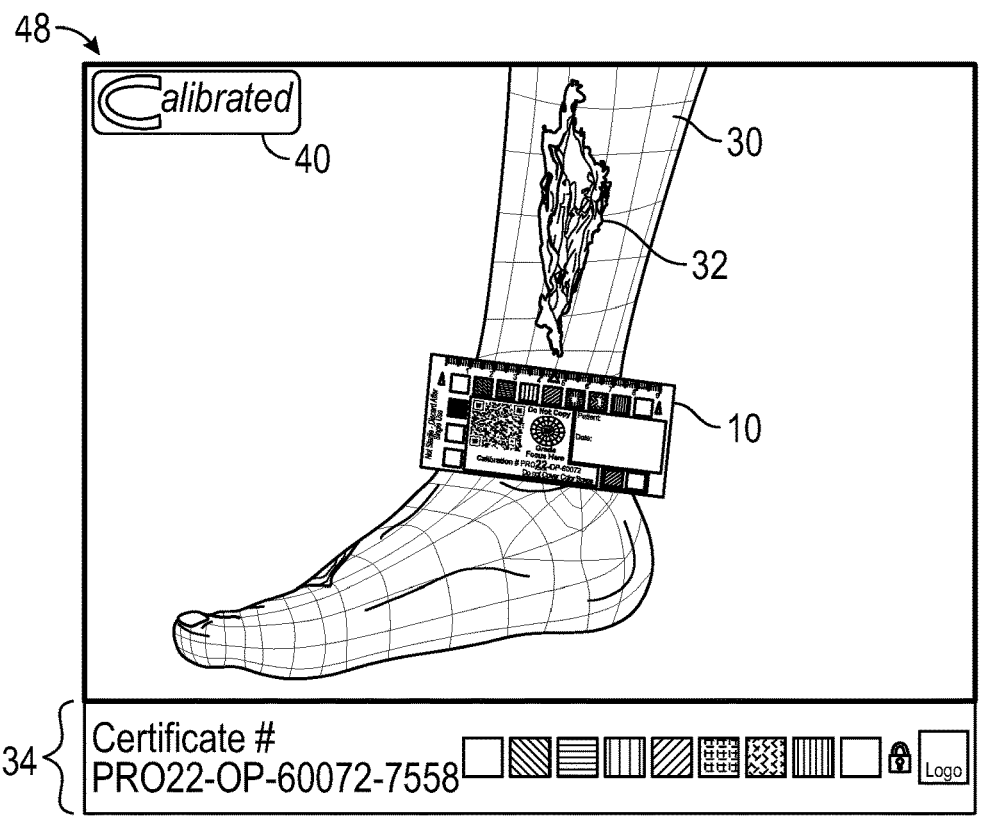
FIG. 8 shows a calibrated three-dimensional image in accordance with the present disclosure.

In a preferred embodiment, to construct a three-dimensional model 44 of the subject 30, the method includes generating point cloud data relating to the subject of each captured two-dimensional image 42, as best seen in FIG. 7. The point cloud data represent the three-dimensional shape of the subject 30, which includes the three-dimensional contours of the wound 32 of the subject. Point cloud data may be generated by capturing an image or video using a LIDAR-enhanced camera, any camera capable of capturing 3D information such as a camera sold under the trademark TrueDepth® by Apple, Inc., or any other suitable type of 3D scanner or photogrammetry software program. A three-dimensional model 44 of the subject may then be constructed utilizing the point cloud data. To construct the three-dimensional model 44, the point cloud data may be converted into a surface mesh, such as a polygon mesh, through surface reconstruction methods. Any suitable method for converting point cloud data to a three-dimensional surface mesh may be utilized, including, but not limited to, Delaunay triangulation, alpha shapes, or through a marching cubes algorithm, for instance. As best seen in FIG. 7, one or more two-dimensional images 42 may then be applied to the three-dimensional model 44 to produce the three-dimensional image 48 of the subject, as seen in FIG. 8. The three-dimensional image 48 also shows the calibration slate 10 that appears in each two-dimensional image 42 of the subject 30. As used herein, a two-dimensional image may be "applied" to a three-dimensional model by graphically laying a visual two-dimensional skin onto a surface defined by the three-dimensional model, which may include interpolation of two-dimensional image data to determine what image data may be duplicative and what data may be missing when applying a plurality of two-dimensional images to a three-dimensional model to produce a three-dimensional image of the subject, or other suitable methods of using two-dimensional images and three-dimensional models to produce three-dimensional visual representations.

Figure 5A:
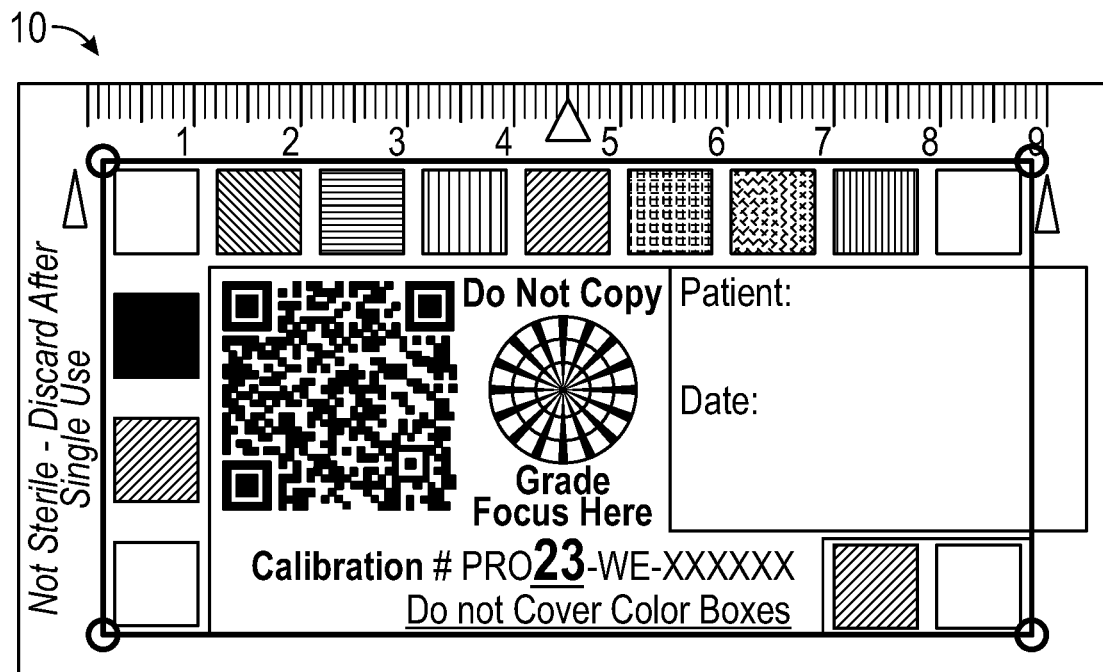
FIG. 5A shows a calibration slate that may be utilized for calibrating three-dimensional images in accordance with the present disclosure.
Figure 5B:
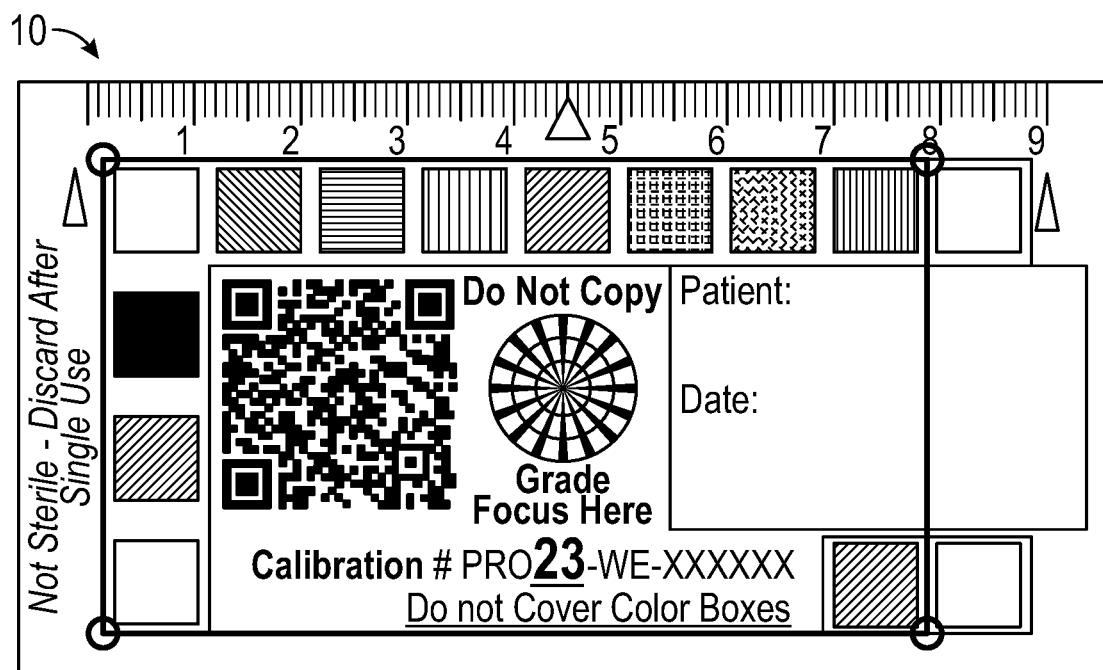
FIG. 5B shows a calibration slate that may be utilized for calibrating three-dimensional images in accordance with the present disclosure.
Figure 5C:
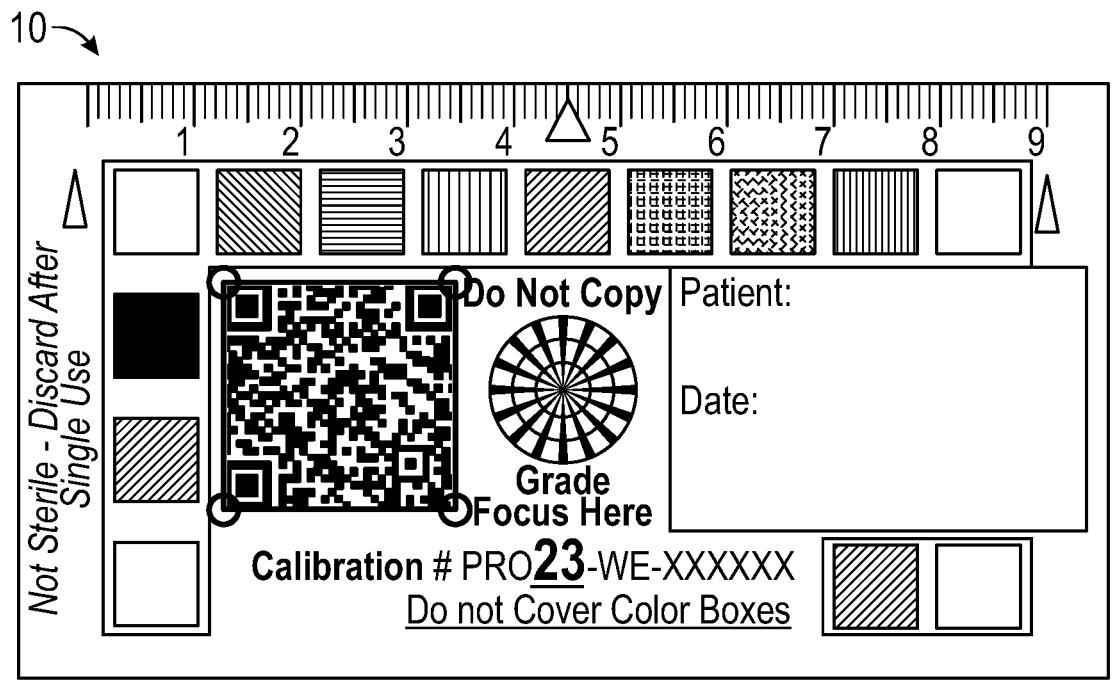
FIG. 5C shows a calibration slate that may be utilized for calibrating three-dimensional images in accordance with the present disclosure.
Figure 5D:
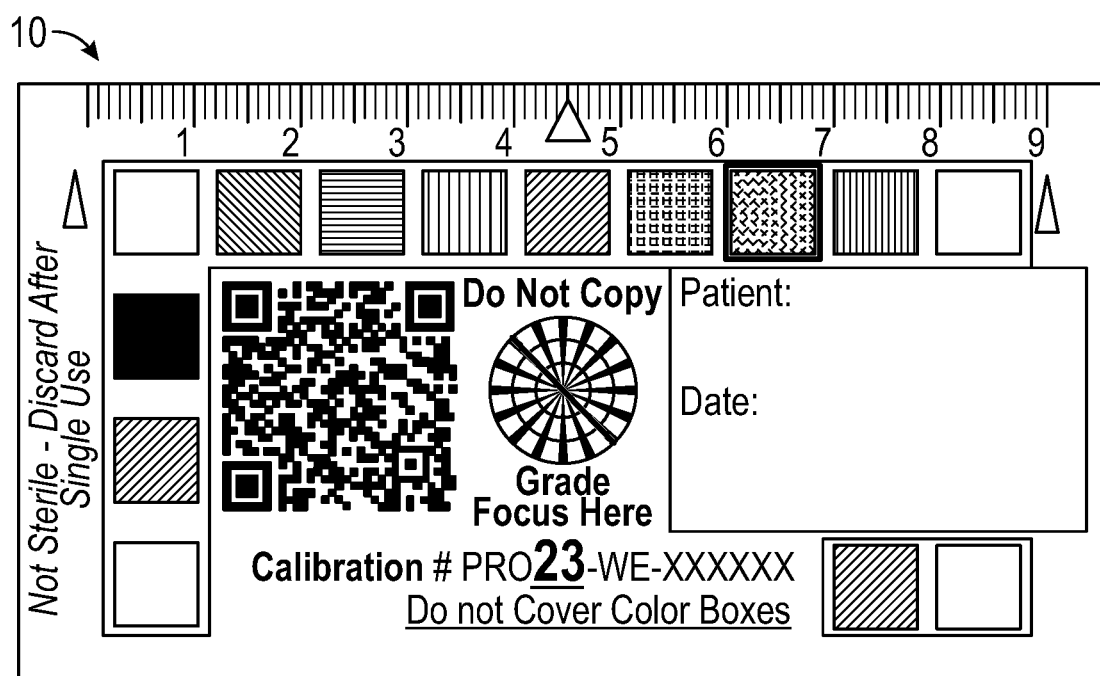
FIG. 5D shows a calibration slate that may be utilized for calibrating three-dimensional images in accordance with the present disclosure.

In some embodiments, the three-dimensional image 48 may be constructed utilizing a plurality of two-dimensional images 42 of the subject 30, which may be captured from varying angles relative to the subject, each including the same calibration slate 10 in the image, which is preferably attached to the subject. To correct skew that may occur when capturing two-dimensional images at an angle to the subject 30, the scale of objects relating to the subject and appearing in each of the two-dimensional images 42, such as the patient wound 32, may be determined based on known measurements of one or more objects printed on the calibration slate 10 that appears in each of the two-dimensional images. The calibration slate has numerous objects printed on the slate having known measurements that may be utilized to this end. FIGS. 5A-5D identify some example objects that may be utilized. For instance, FIG. 5A shows known measurements extending to the four corners of the complete color set 16, while FIG. 5B shows measurements extending to all but two of the color squares 16a-16i, or chips, on the calibration slate, with the two chips farthest to the right of the slate excluded from the measurement, which in this embodiment are both white chips 16b. In this case, these known measurements, which are truncated from the dimensions of the full color set, may be utilized if the chips farthest to the right on the slate are not adequately detected by the image recording device 104. In some cases, areas of the slate 10 having smaller known measurements may be utilized. For instance, in FIG. 5C, the dimensions of the bar code 14 are utilized. Even the dimensions of a single chip, as shown in FIG. 5D, may be utilized, which in this case is an orange chip 16h. In other cases, the known diameter of the focus chart 18 may be utilized. In a preferred embodiment, the system 100 may utilize combinations of such known measurements of objects printed on the calibration slate for skew detection and correction.

In one embodiment, the scale of objects in the image, such as the wound 32, may be determined by counting pixels or other photographic elements composing the object of known size from the calibration slate 10 shown in the image. By comparing the known measurements of the color set 16, any combination of chips within the color set, the QR code 14, the focus chart 18, or some other feature printed on the slate, or combinations thereof, to the number of pixels or other photographic elements of the object shown in the captured image 42, such as the wound 32, the system 100 may determine the scale or ratio of the known metric to the metrics of the captured image for which the scale is to be determined. Additionally, the distance measured may be a pattern or combination of objects on the calibration slate or the outer edges of the slate itself.

Figure 6:
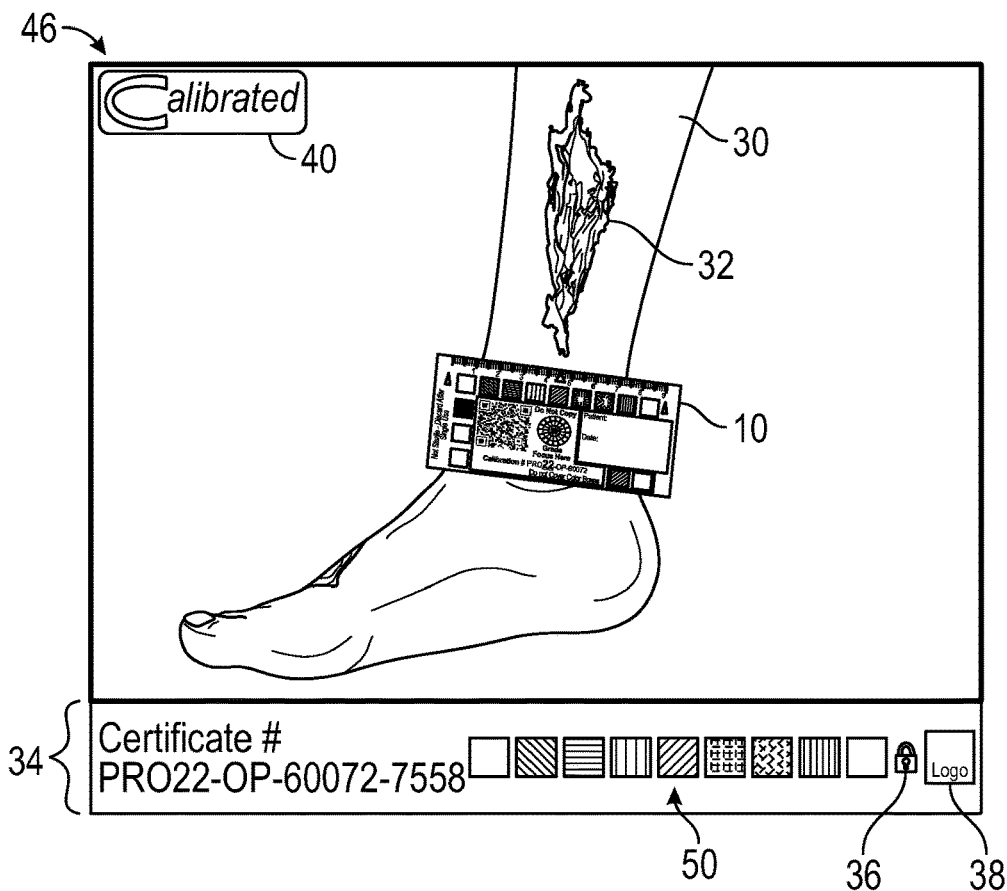
FIG. 6 shows a calibrated two-dimensional image in accordance with the present disclosure.

To color calibrate a three-dimensional image, the present method preferably begins by first using the image recording device 104 to capture one or more two-dimensional images 42 of the subject 30 with the same calibration slate 10 being shown in each image adjacent to the subject, as best shown in FIGS. 6 and 7. In a preferred embodiment, the two-dimensional images are first color calibrated before producing the three-dimensional image. Alternatively, the three-dimensional image may first be produced utilizing the one or more two-dimensional images and then calibrated. To calibrate the captured images, the system 100 may then measure numeric color values from one or more colors 16 in the color chart printed on the calibration slate 10 that appears in each captured image 42. Thus, because the calibration slate 10 appears within the image 42, as shown in the captured two-dimensional image 42 as shown in FIGS. 7 and 14 and the calibrated two-dimensional image 46 as shown in FIG. 6, color values are measured from the captured image itself 42 when measuring the color values from the calibration slate 10. The system 100 may be configured to locate and identify the calibration slate 10 within the borders of the captured image 42, which may be uploaded or transferred to the system 100 from the image recording device 104, based on identification of one or more printed elements on the slate. The system 100 may then further identify discrete colored squares 16 or other areas of the color chart on the slate 10 and further associate known color values for the slate 10 with individual respective colors 16a-16i of the color chart as shown in the captured image 42. The system 100 may then measure color values from one or more of the colors 16 of the color chart as shown in the image 42 as captured by the image recording device 104. The captured image 42 is preferably a digital photograph or other type of electronic representation, and the system 100 may identify and measure color values for each individual pixel or other similar individual picture elements of the portion of the electronic image located within the color chart 16 to measure color component intensities of individual colors, such as red, blue, and green (RBG color values), or other colors such as grey 16c, white 16b, green 16d, cyan 16e, magenta 16f, yellow 16g, orange 16h, or black 16a.

In addition, after locating and identifying the calibration slate 10 shown in the captured image 42, the system 100 may then read the print run number 12 on the calibration slate 10 and associate the print run number 12 with a batch of printed calibration slates that includes the specific calibration slate 10 appearing in the image 42. Because each calibration slate in the batch, including the slate appearing in the image 10, is substantially similar, the numeric color values measured from the color chart 16 shown in the captured image 42 have corresponding known numeric color values associated with the batch of calibration slates. The measured numeric color values from the color chart 16 shown in the image 42 may then be compared to the corresponding known numeric color values. Based on this comparison, the system 100 may calculate a variance between the numeric color values measured from the image 42 to be calibrated and the corresponding known numeric color values. The system 100 may then calculate a calibration factor based on the variance. Once a calibration factor has been determined, each image 42 may be color calibrated based on the calibration factor by adjusting the colors of the image by applying the calibration factor to numeric color values measured from the image. To this end, the system 100 may measure color values for each individual pixel or other similar individual picture elements of the entire captured image 42 to measure color component intensities throughout the image and then adjusting the color values of each pixel of the captured image 42 according to the calibration factor to calibrate the entire image. FIG. 6 shows a color calibrated and certified two-dimensional image 46 of a subject 30 with a wound 32 on the leg of a patient.

Because the calibration slate 10 with colors 16 is placed within the same area of the captured image, the colors on the slate are subject to the same unknown conditions of the environment (including lighting, camera settings, and camera software manipulation). Thus, the system 100 can compare measured color values from the image (from the calibration slate portion of the image) with known standards from the printed calibration slates to determine the calibration factor that can be applied to the entire image including both the subject 30 and the slate 10. Any single color from the color chart printed on the slate may be used to calibrate the entire image, or more than one color may be used. In one embodiment, a medium grey and/or a white may be utilized. Both white and grey are a blend or mix of all colors and are more noticeable to the eye when changed as compared to black because of its density of color. For instance, if a grey was known to have a same value of 125 in red, green, and blue (RGB), then it would be neutral grey that is evenly mixed of all three. Likewise, if the grey color was in the middle of the gray scale, then it would contain a rich amount of data in the middle of both the visible RGB scale and the grey scales, thus making it a good candidate for calibration of the image.

In one preferred embodiment, the system 100 may utilize the RGB color space for calibration. Using the example of a grey 16c color from the color chart 16 having known RGB values of 125 for each of red, green, and blue, the system 100 can then measure the RGB color values of the grey 16c chip of the calibration slate 10 as it appears within the captured image. If the measured color values of the grey chip as captured in the image are, for example, 144 for red, 119 for green, and 131 for blue, then the system 100 can compare the known and measured color values in order calculate a calibration factor for each of the red, green, and blue color values. The calibration factor may be calculated, for example, by calculating the ratio of the measured color value to the known color value for each RGB value. In this example, the calibration factor for red would be 1.15, the calibration factor for green would be 0.95, and the calibration factor for blue would be 1.05. The system 100 may then measure color values from each pixel or other unit of the captured image and apply the calibration factor for each RGB color value to the measured RGB color values that are measured from the captured image. For example, if the system measured RGB color values of 154, 180, and 20 from a pixel of the captured image, then the system can apply each of the RGB calibration factors to the measured RGB values of that pixel, which would result in each of the measured RGB values of that pixel being adjusted to 177, 171, and 21, respectively, to color calibrate the image. This example utilizes the RGB color space, though it should be understood by one of skill in the art that different color spaces may be utilized and that any colors having known color values within that space may be utilized for color calibration. Further, it should be understood by one of skill in the art that one or more calibration factors may be calculated based on different mathematical relationships between known and measured color values and still fall within the scope of the present disclosure.

Although any single known color may be used for calibration, in some embodiments, certain colors may be selected as having particular relevance to the subject, such as red for medical subjects with blood vessels present, which may make certain colors better candidates for medical-related image calibration. For instance, certain colors may be selected for particular relevance to the subject and the process to maximize the data, outcome, and ability for the user to identify items of value in the medical field. For example, yellow, magenta, orange, and red are all common in many medical subjects and often correlate to diagnostic characteristics such as red indicating edema, infection, or granulated tissue with good blood flow. Yellow is often the color of slough or puss, which is generally comprised of dead white blood cells. Wound tissue having a black color is typically indicative of necrotic tissue. Therefore, these colors are likely relevant to a medical subject. If these colors are calibrated and appear to match their corresponding known colors once the image is calibrated, than this would indicate that those colors in the subject image are likewise presented accurately. Alternatively, if the colors of the captured image are calibrated to within a predetermined tolerance or margin of error from the known color values, then the image may be determined to be color calibrated.

Figure 9:
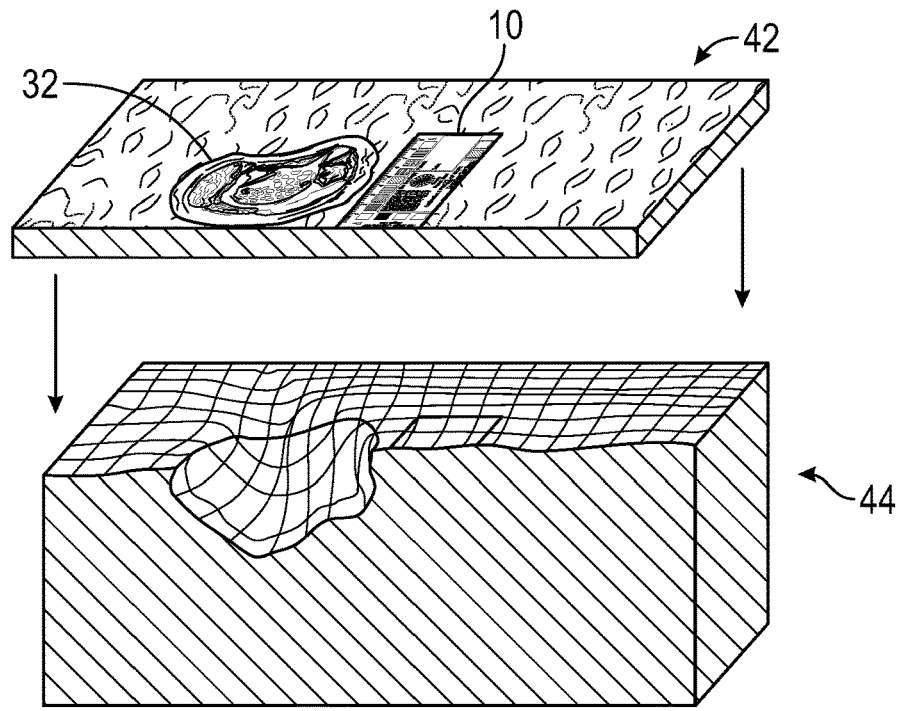
FIG. 9 shows a three-dimensional model of a subject in accordance with the present disclosure.

Next, a three-dimensional image may be produced utilizing the one or more two-dimensional images 42, preferably also utilizing point cloud data. As best seen in FIGS. 7 and 9, one or more two-dimensional images 42, which have preferably first been color calibrated in accordance with the present method to produce a color calibrated two-dimensional image 46, may be applied to a three-dimensional model 44 constructed utilizing the point cloud data relating to the subject 30 to produce a color calibrated three-dimensional image 48. FIG. 8 illustrates the three-dimensional image 48 within a graphical display after the image has been color calibrated and certified, as indicated by the lower certification display 34. Once the calibration of the three-dimensional image 48 is complete, the user will have a three-dimensional visual representation that accurately shows the colors of the patient wound 32 regardless of any external factors that may affect the visual appearance of the wound, thereby giving medical professionals necessary information for accurately diagnosing and evaluating the patient. In addition, the user may manipulate the three-dimensional image 48 to view an accurate visual representation of the contours of the wound 32 in three dimensions.

Figure 10:
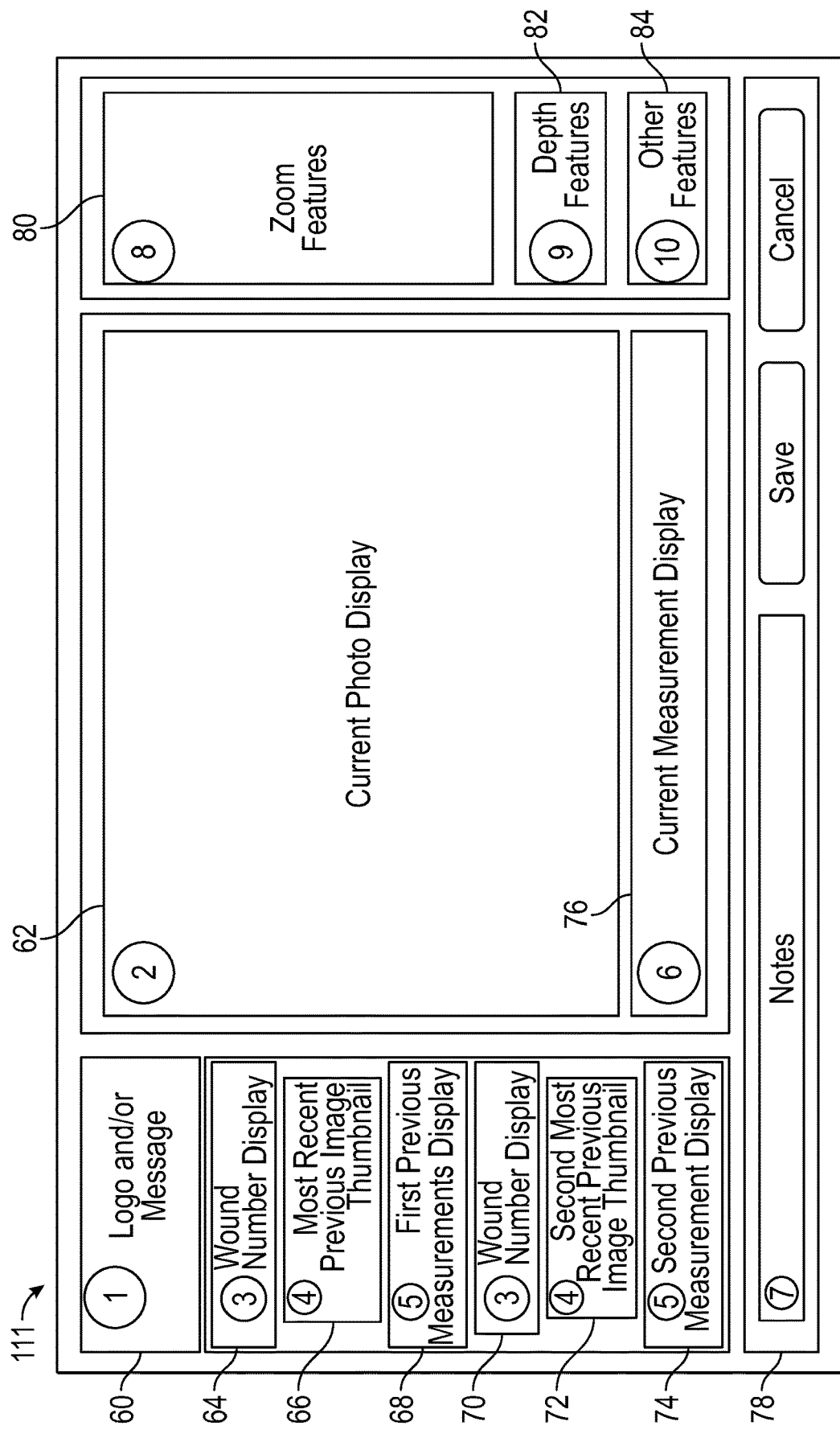
FIG. 10 shows a graphical user interface that may be used with a system for calibrating three-dimensional images in accordance with the present disclosure.
Figure 11:
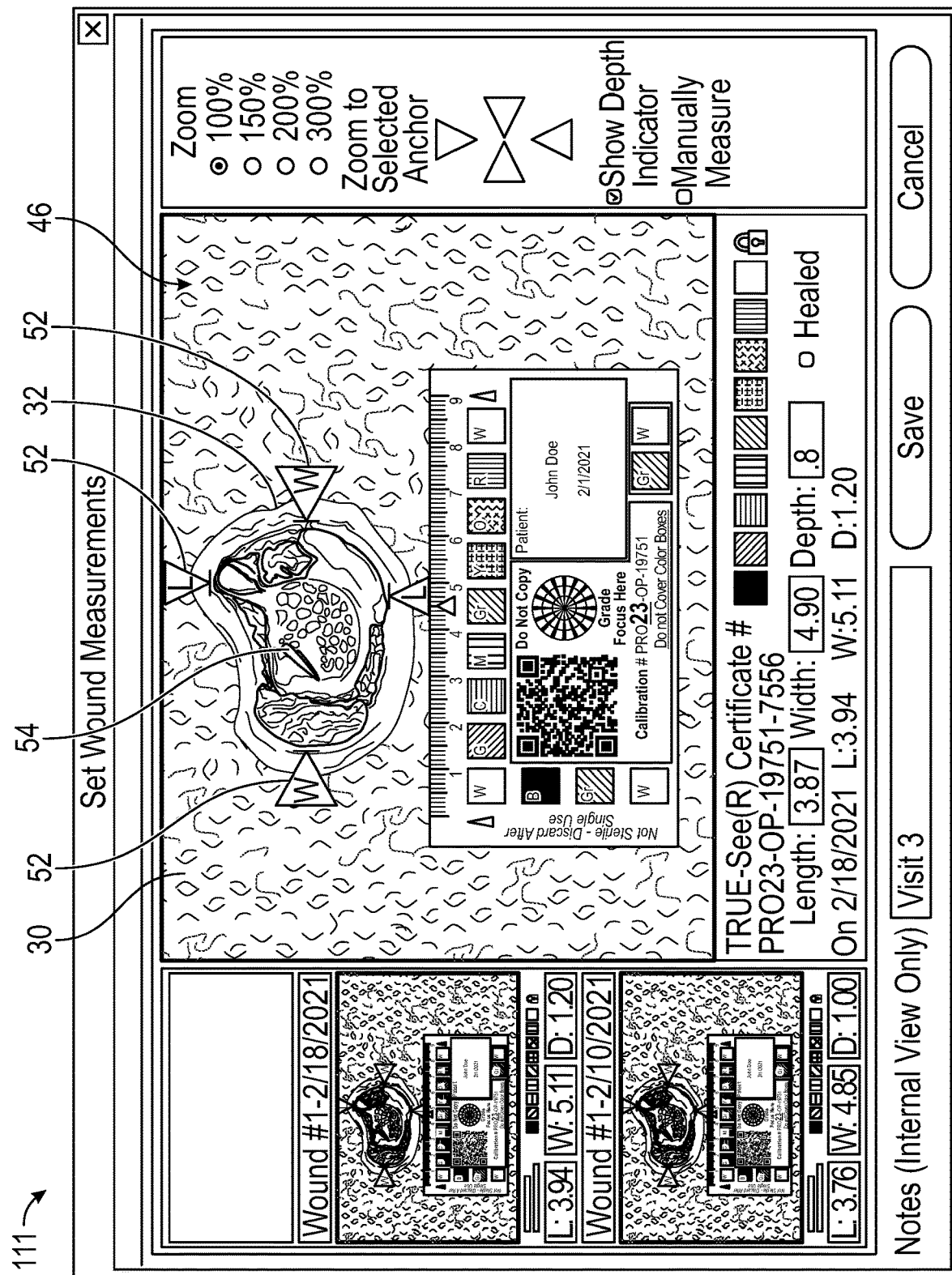
FIG. 11 shows a graphical user interface showing a calibrated two-dimensional image in accordance with the present disclosure.
Figure 12:
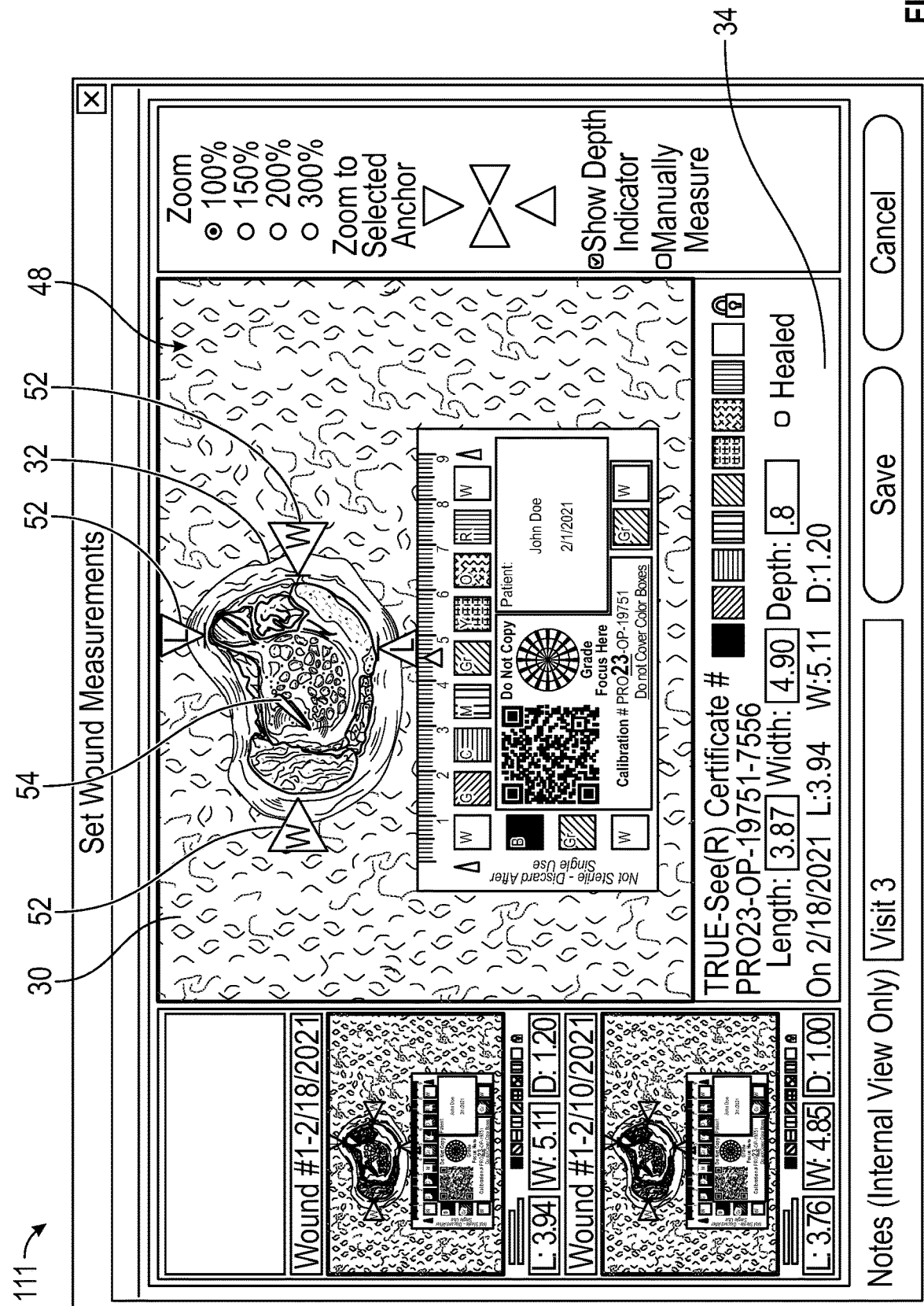
FIG. 12 shows a graphical user interface showing a calibrated three-dimensional image in accordance with the present disclosure.

FIG. 9 illustrates another example of applying a two-dimensional image 42 of a wound 32 to a three-dimensional model 44 to produce a three-dimensional image 48. As shown in FIG. 9, the wound 32 has a depth that is represented by the three-dimensional model 44. This wound depth will change with time as the healing process occurs. FIG. 10 illustrates an example graphical user interface 111 that may be utilized for a user 102 to interact with the system 100. FIG. 11 illustrates the two-dimensional image shown in FIG. 9 within the graphical user interface 111 after the image 46 has been color calibrated. FIG. 12 illustrates a color calibrated three-dimensional image 48 produced by applying the two-dimensional image 42 to the three-dimensional model 44 as shown in FIG. 9. The color calibrated three-dimensional image 48 is shown within the same graphical user interface 111 after the image has been color calibrated. FIG. 12 illustrates the three-dimensional image 48 from one specific angle, though the three-dimensional image 48 may be rotated, tilted, or otherwise manipulated within the graphical user interface 111 to allow the user 102 the ability to view the contours of the wound in three dimensions and to see the wound 32 with calibrated colors.

Figure 13:
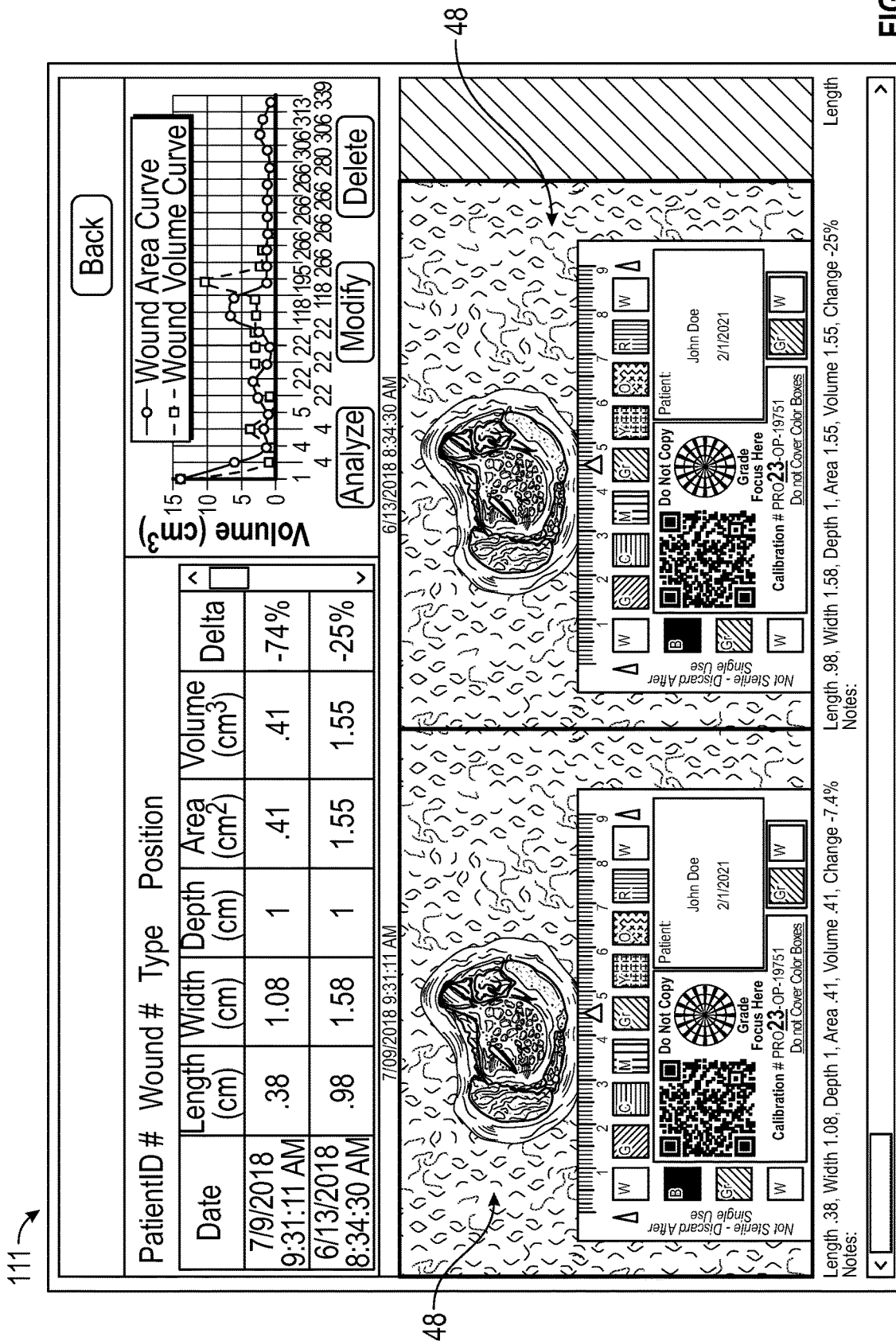
FIG. 13 shows a graphical user interface showing multiple calibrated three-dimensional images illustrating changes in a patient wound over a period of time in accordance with the present disclosure.

FIG. 10 illustrates an example graphical user interface 111 having multiple internal windows before being populated with images or videos and other information relating to the subject 30. Window 60 provides a space for a business logo and/or a message to a user 102 relating to the system 100. Window 62 is the primary window in which images or videos may be displayed, including color calibrated two-dimensional 46 and three-dimensional images 48 or videos, as well as captured images 42 or videos. Three-dimensional images 48 may be manipulated by the user 102 within this window 62. Windows 66 and 72 may display thumbnail views of previously calibrated images of the subject 30 at different time intervals, as indicated by the date shown in windows 64 and 70, which also display a wound number associated with the wound 32. Additional iterations of the present method may be performed at various time intervals to consecutively produce additional calibrated three-dimensional images 48 or videos of the same subject 30 to observe changes in the subject in three dimensions over a period of time. Each additional calibrated three-dimensional image 48 includes a unique calibration slate 10 used for each iteration of the method. Thus, the additional images are each independently color calibrated using a different slate 10 each time. Each of the calibrated three-dimensional images 48 of the subject 30 may then be compared to a preceding calibrated image 48 to qualitatively determine how the subject 30 has changed over time. The system 100 may allow the user to view multiple three-dimensional images 48 of the same subject 30 sorted by date within the graphical user interface 111, as shown in FIG. 12. The system 100 preferably includes an additional interface 111 specifically for viewing all iterations of the calibrated images 48, as shown in FIG. 13, which illustrates two calibrated three-dimensional images 48 of a subject 30 that were produced on different dates, which are labeled above each three-dimensional image so that a medical professional may view changes in the wound side-by-side and scroll though all iterations to evaluate progress in healing. As shown in FIG. 13, this interface 111 may show additional information relating to the wound, such as information relating to the dimensions of the wound.

The graphical user interface 111 shown in FIG. 10 may also have a window 80 having zoom view features for enabling a user 102 to manipulate the image shown in the primary window 62. The interface 111 may also include windows 82, 84 relating to depth features and other various features of the calibrated image. The interface 111 may also have a window 78 for adding general notes relating to the patient and/or images.

The system 100 may also be used to measure the physical parameters, including depth, of the wound 32, which allows the user 102 to monitor how the wound changes with time, including both the color of the wound and the depth or other parameters of the wound. Thus, the present system 100 provides a complete and accurate visual representation of wounds 32 or skin conditions for medical professionals and provides the ability to monitor how these characteristics change with time. As shown in FIGS. 11 and 12, the interface 111 may include movable anchor points 52 that may be used to measure certain dimensions of the wound, such as length and width. The measurements of wound parameters may be calculated according to determinations of the scale of objects in the image, such as the wound, based on known measurements of objects printed on the calibration slate 10 such as the ruler 22 or bar code 14. When moving the anchor points 52 to the appropriate positions, the system 100 may automatically display measurements in windows 68, 74, and 76, which display different iterations of the calibrated images. Measurement information may also be automatically displayed in the interface 111 shown in FIG. 13, which may include graphical representations showing how an area and a volume of the wound change with time to graphically assess wound progress. Wound volume may be based on the depth of the wound, which may be calculated based on three-dimensional model 44 data. As shown in FIGS. 11 and 12, the interface 111 may also include a movable depth indicator 54, which the user 102 may position at a location on the image of the wound to indicate the wound depth at that location. The depth indicator 54 may also be used to mark locations for other purposes, such as the location of a particular procedure performed on the patient. These locations may be saved for later viewing. The depth indicator 54 may also be used to indicate any three-dimensional point on the three-dimensional image 48. The visibility of a depth indicator 54 may be turned on or off by the user.

Before using a calibration slate 10 to calibrate an image, the system 100 may also be used to read the unique identifier 14, which is preferably a machine-readable bar code, and validate the specific calibration slate 10 used based on the unique identifier 14 to verify that the calibration slate 10 has not been previously used prior to capturing images 42 or videos of the subject 30, which prevents potential cross-contamination between patients. The bar code 14 on each unique slate 10 links to information related to each slate, and the system 100 may be configured to determine whether a specific slate has been used in a calibrated image or video and alert a user if the slate has been previously used so that each individual slate is used only once. Validating the calibration slate 10 may also indicate that the slate 10 is an original slate from a known source. Validating the calibration slate 10 may also indicate that the slate 10 is not being used in a restricted manner, which may be indicated by validating who is using the slate, where the slate is being used, and when the slate is being used.

After calibrating an image 48 or video, the system 100 may also be used to certify that the image or video has been processed and properly calibrated. To certify the image 48 or video, the system 100 may assign a unique number to the image or video after processing and calibration and then embed the unique number within the color calibrated image or video. The system 100 may then certify the color calibrated image or video by reading the unique number. The unique certification number may be visually displayed or, optionally, may not be displayed. In a preferred embodiment, as best seen in FIGS. 6 and 8, the system 100 may graphically attach or display a certification bar 34, which may provide certain information relating to the image or video, to the calibrated image 46, 48 or video that includes the calibration slate 10. The certification bar 34 preferably includes a second color chart 50, wherein the second color chart 50 comprises a set of colors having known numeric color values. Each color in the set of colors is substantially similar to a respective corresponding color associated with the batch of calibration slates from which the slate 10 in the image originates. Because the second color chart 50 is not part of the original image, attaching this second color chart allows a user 102 to make a qualitative visual comparison of the colors on the second color chart 50 to the colors on the slate 10 in the image to qualitatively assess the quality of the color calibrated image or video instantaneously. In addition, as shown in FIGS. 6 and 8, after calibrating the image or video the system 100 may add the unique certification number to the attached certification panel 34 that provides a confirmable indication that the image or video is certified as being processed and calibrated by the system 100. The certification number is preferably machine-readable and the image or video may be automatically certified by reading the unique certification number. The system 100 may also add a hash code to each certified image or video to provide an indication that the image or video has not been altered or tampered with in any way. The hash code may be visually indicated by an element in the certification bar 34 such as a lock icon 36 indicating that the image or video may not be altered. Alternatively, other suitable security features that prohibit and/or detect alterations to the certified image or video may be utilized to prevent unauthorized alterations to the image or video. The certification bar 34 attached to the certified image or video preferably also includes a logo box 38, which may be used to add a logo of a client utilizing the system 100 to visually indicate a client's identity to a system administrator. The certification bar 34 may be toggled on and off by the user.

Figure 22:
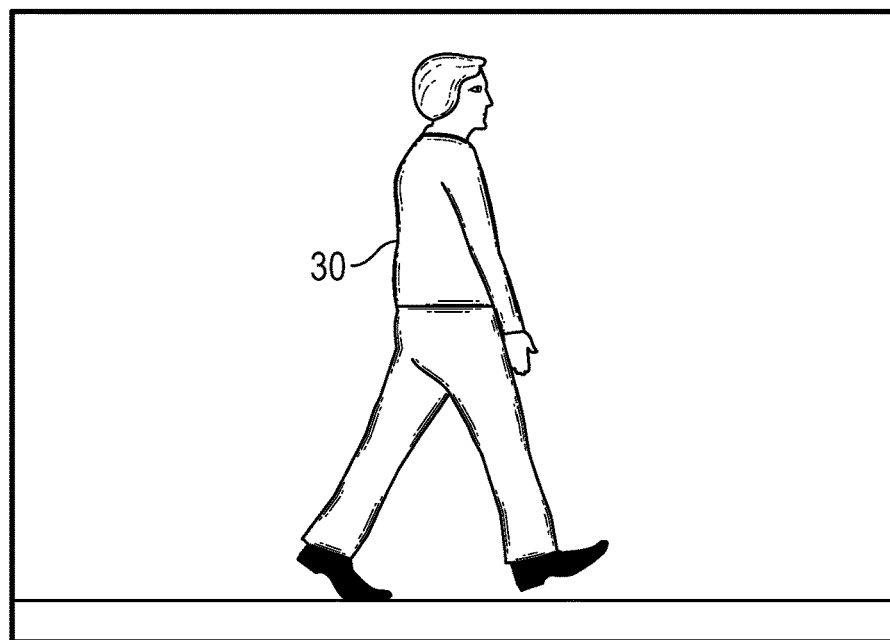
FIG. 22 shows a captured frame of a video before calibration.
Figure 23:
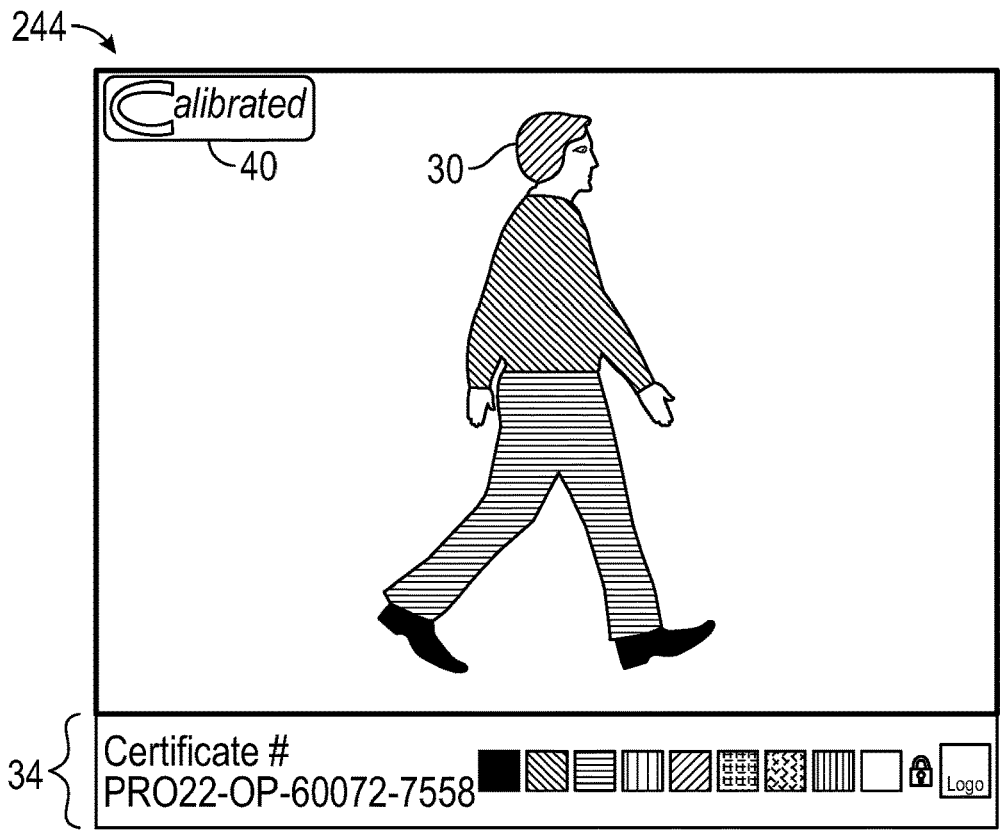
FIG. 23 shows a calibrated frame of a video without a calibration slate and with color segmentation in accordance with the present disclosure.

In a preferred embodiment, as shown in FIGS. 6 and 8, the system 100 may additionally add a watermark 40, which is preferably shown in an upper or lower corner of a calibrated image or video. The watermark 40 may indicate "calibrated" for a calibrated image, as shown in FIGS. 6 and 8, or a calibrated video, as shown in FIGS. 22 and 23. In other cases, the watermark 40 could indicate that an image or video is not calibrated, or it could indicate any improper use of the system 100, such as the use of an invalid calibration slate 10 or if a user has an invalid license. The watermark 40 may be added automatically by the system 100 based on the status of the image or video shown in the interface 111. As used herein, a "watermark" may refer to any visible security feature embedded in the image or video.

Before using any calibrations slates 10 from a batch of printed slates, the system 100 may verify that all slates within the batch are substantially similar to ensure that the print run of slates produced slates with colors having consistent color values. Corresponding numeric color values may be measured directly from a plurality of respective slates within the batch. A variance may then be calculated between the numeric color values measured from each of the slates. The plurality of slates within the batch would be verified to be substantially similar if the variance is within an acceptable range, which would indicate that each individual slate 10 of the batch is suitable for use in calibrating the color of an image or video.

FIG. 14 illustrates a system 100 that may be used to carry out the present method of producing color calibrated images or videos. As illustrated in FIG. 14, the system 100 generally comprises a recording device capable of capturing still images and/or videos, such as a camera 104, a calibration slate 10, a processor 115 operably connected to the camera 104, a power supply, and a non-transitory computer-readable medium 116 coupled to the processor 115 and having instructions stored thereon, which, when executed, perform method steps of the present method. The camera 104 may be a smartphone or tablet, or another type of device having camera functions. The system 100 may also comprise a computing device 110, wherein said computing device may comprise a user interface 111 that may allow a user 102 to view data of the system 100 and/or cause the system 100 to perform an action via commands input by said user 102. In another embodiment, the system 100 may comprise a database 125 operably connected to the processor 115, which may be used to store patient data 130, image data 135, and, optionally, three-dimensional point cloud data 140 therein. Alternatively, the patient data 130, image data 135, and point cloud data 140 may be stored on the non-transitory computer-readable medium 116. In yet another preferred embodiment, a server 120 may be operably connected to the database 125 and processor 115, facilitating the transfer of information between the processor 115 and database 125. Although represented as a single server 120 and database 125 in FIG. 14, it is understood that multiple servers and databases may be used without departing from the inventive subject matter herein.

As used herein, a database 125 refers to a set of related data and the way it is organized. Access to this data is usually provided by a database management system (DBMS) consisting of an integrated set of computer software that allows users to interact with one or more databases and provides access to all of the data contained in the database. The DBMS provides various functions that allow entry, storage and retrieval of large quantities of information and provides ways to manage how that information is organized. Because of the close relationship between the database 125 and the DBMS, as used herein, the term database refers to both a database and DBMS. The database may be operably connected to the processor via wired or wireless connection. The database may be a relational database such that the patient data 130, image or video data 135, and three-dimensional point cloud data 140 may be stored, at least in part, in one or more tables. Alternatively, the database 125 may be an object database such that patient data 130, image or video data 135, and three-dimensional point cloud data 140 may be stored, at least in part, as objects. In some instances, the database 125 may comprise a relational and/or object database and a server dedicated solely to managing the patient data 130, image or video data 135, and three-dimensional point cloud data 140 in the manners disclosed herein.

As depicted in FIG. 14, one embodiment of the system 100 may comprise a server 120. Although shown as a single server in FIG. 14, a server may, in some implementations, be implemented as multiple devices interlinked together via a network, wherein the devices connected to the network may be distributed over a large geographic area and performing different functions or similar functions. For instance, two or more servers may be implemented to work as a single server performing the same tasks. Alternatively, one server may perform the functions of multiple servers. For instance, a single server may perform the tasks of a web server and an indexing server. Additionally, it is understood that multiple servers may be used to operably connect the processor 115 to the database 125 and/or other content repositories. The processor 115 may be operably connected to the server 120 via wired or wireless connection. Types of servers that may be used by the system include, but are not limited to, search servers, document indexing servers, and web servers, or any combination thereof.

Search servers may include one or more computing entities designed to implement a search engine, such as a documents/records search engine, general webpage search engine, etc. Search servers may, for example, include one or more web servers designed to receive search queries and/or inputs from users, search one or more databases in response to the search queries and/or inputs, and provide documents or information, relevant to the search queries and/or inputs, to users. In some implementations, search servers may include a web search server that may provide webpages to users, wherein a provided webpage may include a reference to a web server at which the desired information and/or links are located. The references to the web server at which the desired information is located may be included in a frame and/or text box, or as a link to the desired information/ document. Document indexing servers may include one or more devices designed to index documents available through networks. Document indexing servers may access other servers, such as web servers that host content, to index the content. In some implementations, document indexing servers may index documents/records stored by other servers connected to the network. Document indexing servers may, for example, store and index content, information, and documents relating to user accounts and user-generated content. Web servers may include servers that provide webpages to clients. For instance, the webpages may be HTML-based webpages. A web server may host one or more websites. As used herein, a website may refer to a collection of related webpages. Frequently, a website may be associated with a single domain name, although some websites may potentially encompass more than one domain name. The concepts described herein may be applied on a per-website basis. Alternatively, in some implementations, the concepts described herein may be applied on a per-webpage basis.

The processor 115 may comprise any type of conventional processor or microprocessor that interprets and executes computer readable instructions. The processor 115 is configured to perform the operations disclosed herein based on instructions stored within the system 100. The processor 115 may process instructions for execution within the computing entity 110, including instructions stored in memory or on a storage device, to display graphical information for a graphical user interface (GUI) 111 on an external peripheral device, such as a display. The processor 115 may provide for coordination of the other components of a computing entity 110, such as control of user interfaces 111, applications run by a computing entity, and wireless communication by a communication interface of the computing entity. The processor 115 may be any processor or microprocessor suitable for executing instructions. In some embodiments, the processor 115 may have a memory device therein or coupled thereto suitable for storing the data, content, or other information or material disclosed herein. In some instances, the processor 115 may be a component of a larger computing device. A computing device 110 that may house the processor therein may include, but are not limited to, laptops, desktops, workstations, personal digital assistants, servers, mainframes, cellular telephones, tablet computers, smart televisions, streaming devices, or any other similar device. Accordingly, the inventive subject matter disclosed herein, in full or in part, may be implemented or utilized in devices 110 including, but are not limited to, laptops, desktops, workstations, personal digital assistants, servers, mainframes, cellular telephones, tablet computers, smart televisions, streaming devices, or any other similar device.

As mentioned previously, the processor 115 is configured to perform the operations disclosed herein based on instructions stored within the system 100. In an embodiment, the programming instructions responsible for the operations carried out by the processor are stored on a non-transitory computer-readable medium ("CRM") 116, which may be coupled to the server 115, as illustrated in FIG. 14. Alternatively, the programming instructions may be stored or included within the processor 115. Examples of non-transitory computer-readable mediums 116 include, but are not limited to, magnetic media such as hard disks, floppy disks, and magnetic tape; optical media such as CD ROM discs and DVDs; magneto-optical media such as optical discs; and hardware devices that are specifically configured to store and perform programming instructions, such as read-only memory (ROM), random access memory (RAM), flash memory, and the like. In some embodiments, the programming instructions may be stored as modules within the non-transitory computer-readable medium 116.

As mentioned previously, one embodiment of the system 100 may further comprise a computing device 110 operably connected to the processor 115. A computing device 110 may be implemented in a number of different forms, including, but not limited to, servers, multipurpose computers, mobile computers, etc. For instance, a computing device 110 may be implemented in a multipurpose computer that acts as a personal computer for a user 102, such as a laptop computer. For instance, components from a computing device 110 may be combined in a way such that a mobile computing device is created, such as mobile phone. Additionally, a computing device may be made up of a single computer or multiple computers working together over a network. For instance, a computing device may be implemented as a single server or as a group of servers working together over and Local Area Network (LAN), such as a rack server system. Computing devices may communicate via a wired or wireless connection. For instance, wireless communication may occur using a Bluetooth, Wi-Fi, or other such wireless communication device.

In an embodiment, the system may further comprise a user interface 111. The user interface 111 may be defined as a space where interactions between a user 102 and the system 100 may take place. In a preferred embodiment, the interactions may take place in a way such that a user may control the operations of the system 100, and more specifically, allow a user 102 to capture images or videos of a subject 30, upload and view images or videos of the subject 30, and generate, view, and manipulate two-dimensional or three-dimensional images or videos of the subject 30, which may include a patient wound 32 or other skin condition of the patient, or videos of patient movement or movement of the recording device relative to the patient. A user 102 may input instructions to control operations of the system 100 manually using an input device. For instance, a user 102 may choose to alter or manipulate images or videos presented via displays of the system 100 by using an input device of the system, including, but not limited to, a keyboard, mouse, or touchscreen. A user interface 111 may include, but is not limited to, operating systems, command line user interfaces, conversational interfaces, web-based user interfaces, zooming user interfaces, touch screens, task-based user interfaces, touch user interfaces, text-based user interfaces, intelligent user interfaces, and graphical user interfaces, or any combination thereof. The system 100 may present data of the user interface 111 to the user 102 via a display operably connected to the processor 115.

Information presented via a display may be referred to as a soft copy of the information because the information exists electronically and is presented for a temporary period of time. Information stored on the non-transitory computer-readable medium 116 may be referred to as the hard copy of the information. For instance, a display may present a soft copy of a visual representation of display data via a liquid crystal display (LCD), wherein the hard copy of the visual representation of display data may be stored on a local hard drive. For instance, a display may present a soft copy of user data, wherein the hard copy of the user data is stored within a database. Displays may include, but are not limited to, cathode ray tube monitors, LCD monitors, light emitting diode (LED) monitors, gas plasma monitors, screen readers, speech synthesizers, haptic suits, speakers, and scent generating devices, or any combination thereof, but is not limited to these devices.

In another aspect, a method of color calibrating videos related to the medical field is provided. As used herein, the terms "video," "moving images," or grammatical equivalents thereof may refer to any tangible visual image that moves or provides the effect of apparent motion. A video or moving image may be a series or sequence of frames or images recorded in any medium without or without sound and displayed in rapid succession to produce the optical effect of a continuously moving image over time which produces the optical effect motion. The medium may be chemical, mechanical, electronic, or any other suitable image medium. An electronic video file may include metadata relating to the video displayed when opening the file. The metadata may include multiple different types of data, including, but not limited to, geo-location, device data, and user data. The metadata can be extracted from single images, sequences of images, videos, three-dimensional models, or three-dimensional videos and can be used in association with other image data to verify, track, and analyze the subject in any of these mediums alone or in combination with other methods described herein. A video may also include the augmentation or the combining of additional imagery with an original video as captured by a recording device. In one embodiment, this may include a video of a medical procedure, such as an operation, combined with virtual reality augmentation to measure in real time objects or attributes of a subject. This data or analysis of such data may be provided in real time or in subsequent viewing of the video as augmented or virtual reality elements displayed with the image in a three-dimensional space constructed from or as part of the video.

The method of color calibrating a video comprises first capturing a video 242 of a subject 30 on a recording device 104. The captured video 242 comprises a sequence 246 of frames 248 each comprising a still image 250. One or more of the frames 248 includes a calibration slate 10 appearing in the still image 250 of at least one frame 248 of the sequence 246 of frames of the video 242. The calibration slate 10 has a print run number 12 that identifies a batch of printed calibration slates that includes the calibration slate 10 appearing in the still image 250 and a color chart 16 comprising at least one color. The calibration slate 10 preferably also has a unique identifier 14 that individually identifies the calibration slate 10 appearing in the still image 250. The system 100 may read the unique identifier 14 and validate the calibration slate 10 based on the unique identifier. A numeric color value is measured from a color of the color chart 16 on the calibration slate 10 that appears in the still image 250. The measured numeric color value may then be compared to the corresponding known numeric color value associated with the batch of printed calibration slates that includes the calibration slate 10 appearing in the still image 250 of the frame 248. The individual slate 10 appearing in the frame 248 may be associated with the batch from which it originates by reading the print run number 12 printed on the slate 10. A variance may be calculated between the measured numeric color value and the corresponding known numeric color value, and a calibration factor may be calculated based on the variance. The captured video 242 may then be color calibrated by adjusting one or more captured colors of the still image 250 of each frame 248 of the sequence 246 of frames to produce a color calibrated video 244. To adjust the captured colors of each frame 248, the calibration factor may be applied to a numeric color value measured from the still image 250 of each frame of the sequence of frames. This method may be utilized to color calibrate two-dimensional videos or three-dimensional videos.

As used herein, a "captured video" or "captured color" refers to a video and a color within the video as captured by a recording device before being color calibrated in accordance with the present method. The captured video and captured colors of the video may have been manipulated by software installed on the recording device or other features of the recording device at the time of being captured but have not yet been color calibrated in accordance with the present method.

Figure 22A:
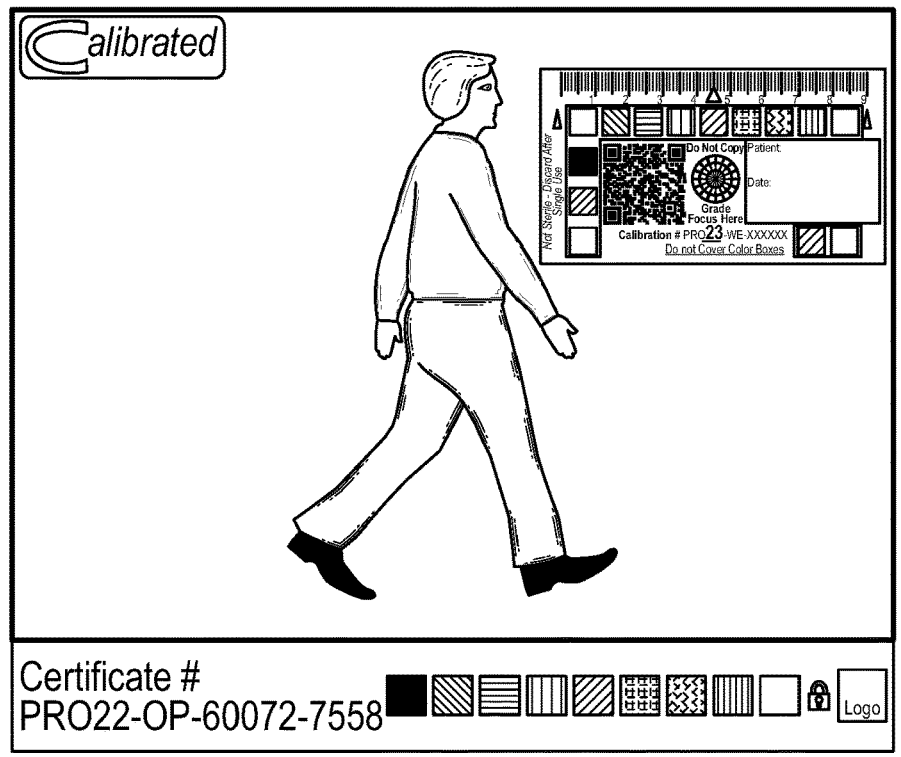
FIG. 22A shows a color calibrated frame of a video in accordance with the present disclosure.
Figure 25:
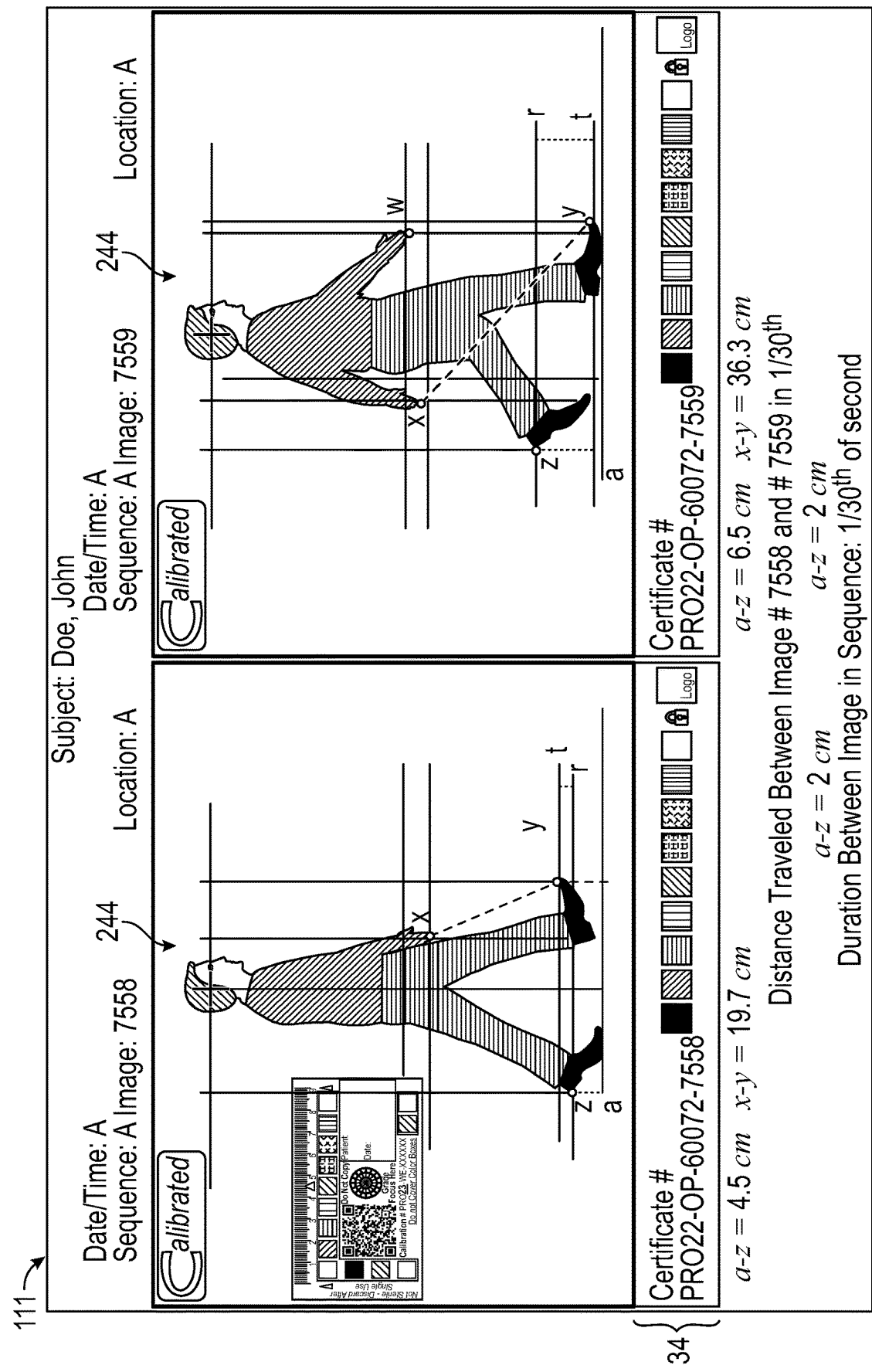
FIG. 25 shows a graphical user interface showing two calibrated frames of a video in sequence with each other with distance measurements in accordance with the present disclosure.
Figure 26:
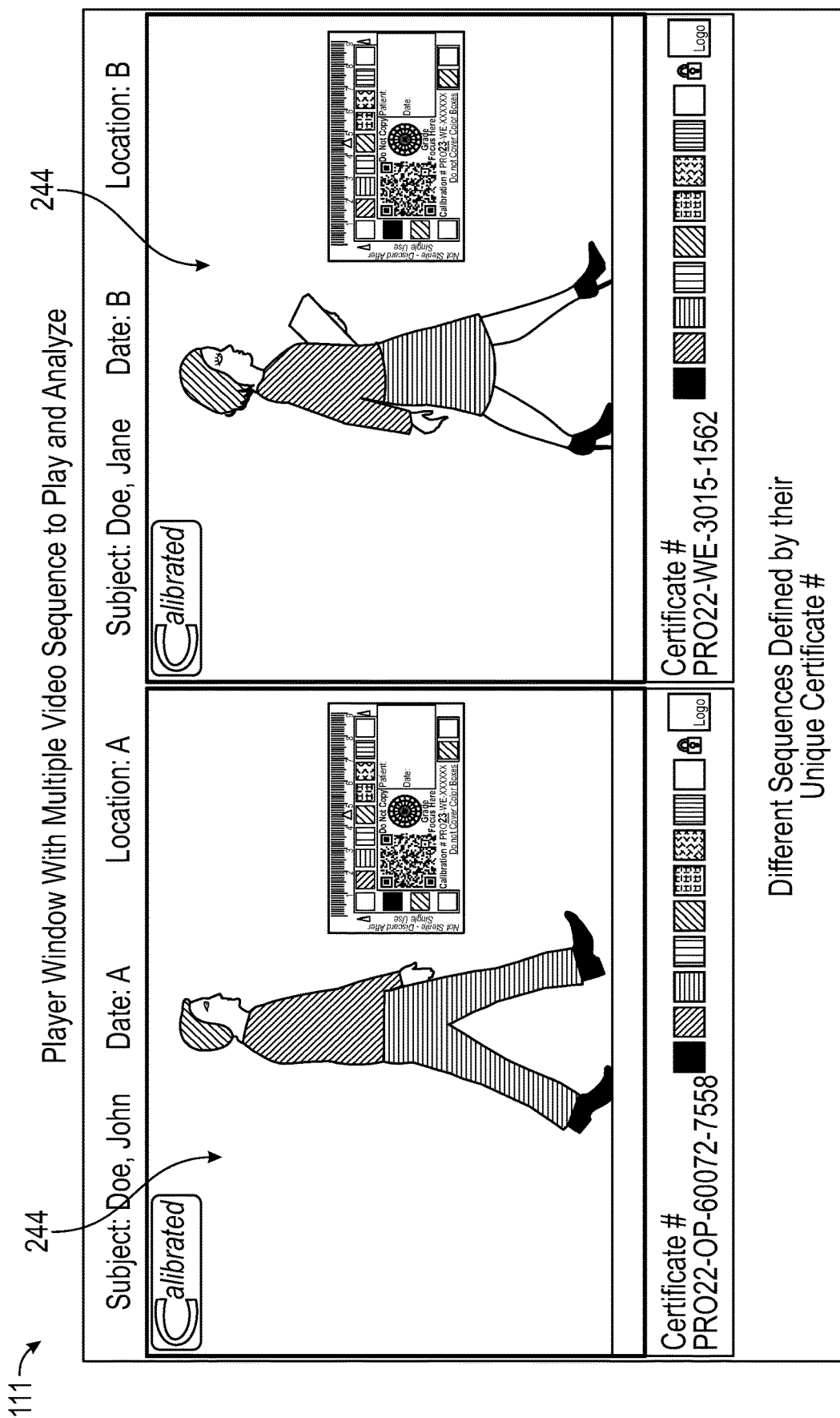
FIG. 26 shows a graphical user interface showing two separate calibrated video sequences in accordance with the present disclosure.

FIG. 22 shows a graphical interface displaying a captured video 242 that has not been calibrated, and FIG. 22A shows a color calibrated video 244 with a calibration slate 10 appearing within a frame 248 of the video 244. FIGS. 25 and 26 illustrate a graphical user interface 111 that may be utilized to view and analyze one or more color calibrated videos 244. After calibrating a video 244, the system 100 may also be used to certify that the video 244 has been processed and properly calibrated. To certify the video 244, the system 100 may assign a unique number to the video 244 after processing and calibration and then embed the unique number within the color calibrated video 244. The system 100 may then certify the color calibrated video 244 by reading the unique number. The unique certification number may be visually displayed or, optionally, may not be displayed. A unique certification number may be assigned to a calibrated video 244 in its entirety or to one or more individual frames 248 for use separate from the entire video.

Figure 23A:
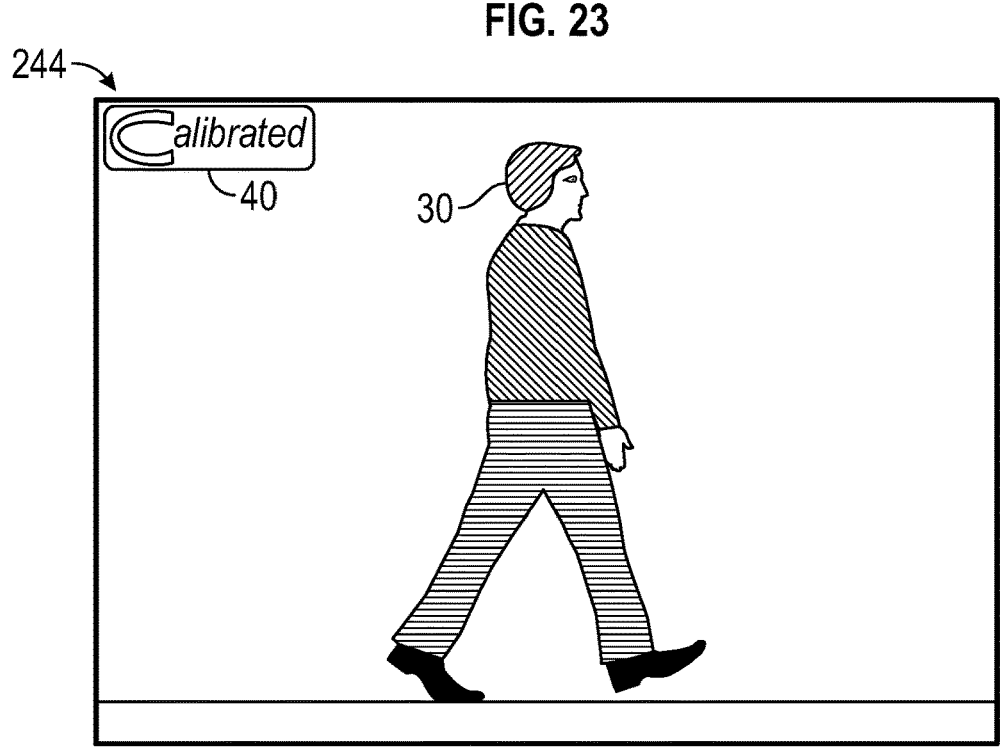
FIG. 23A shows a calibrated frame of a video without a displayed certification in accordance with the present disclosure.

In a preferred embodiment, as shown in FIGS. 22A and 25, the calibrated video 244 preferably includes a certification panel 34 displayed within the interface 111. The certification panel 34 preferably displays a certification number that certifies that the video 244 has been color calibrated by the system 100 and that the color calibrated video 244 has not been altered in any way after calibration. The panel 34 may also include a lock icon 36 to indicate that the video 244 is calibrated and may not be altered. The certification panel 34 preferably also includes a second color chart 50 displayed within the panel 34 for qualitative color analysis of the calibrated video 244. The certification panel 34 is optional and a visual display of the panel 34 may be turned on or off by a user 102. FIG. 23A illustrates a calibrated video 244 with the certification panel 34 turned off. The calibrated video 244 may also include a watermark 40 displayed in the video to indicate that the video 244 has been color calibrated by the system 100.

Calibrated videos 244, as well as images, may be stored as an electronic file that contains data related to the calibrated video 244. The data may be related to the video 244 in its entirety or to one or more individual frames 248 of the video. In a preferred embodiment, a hash code may be embedded within the file. The hash code is designed to change automatically if the data related to the video file is altered in any way, including any alterations to the calibrated colors of the video. The color calibrated video 244 may optionally include a graphically displayed icon, such as the lock icon 36, that visually indicates that the hash code has not changed. Individual frames 248 of the video 244 may be removed from the sequence 246 and assigned a new hash code so that individual frames 248 may be displayed outside the sequence 246 while maintaining confirmation that the removed frame 248 has not been altered.

Figure 24:
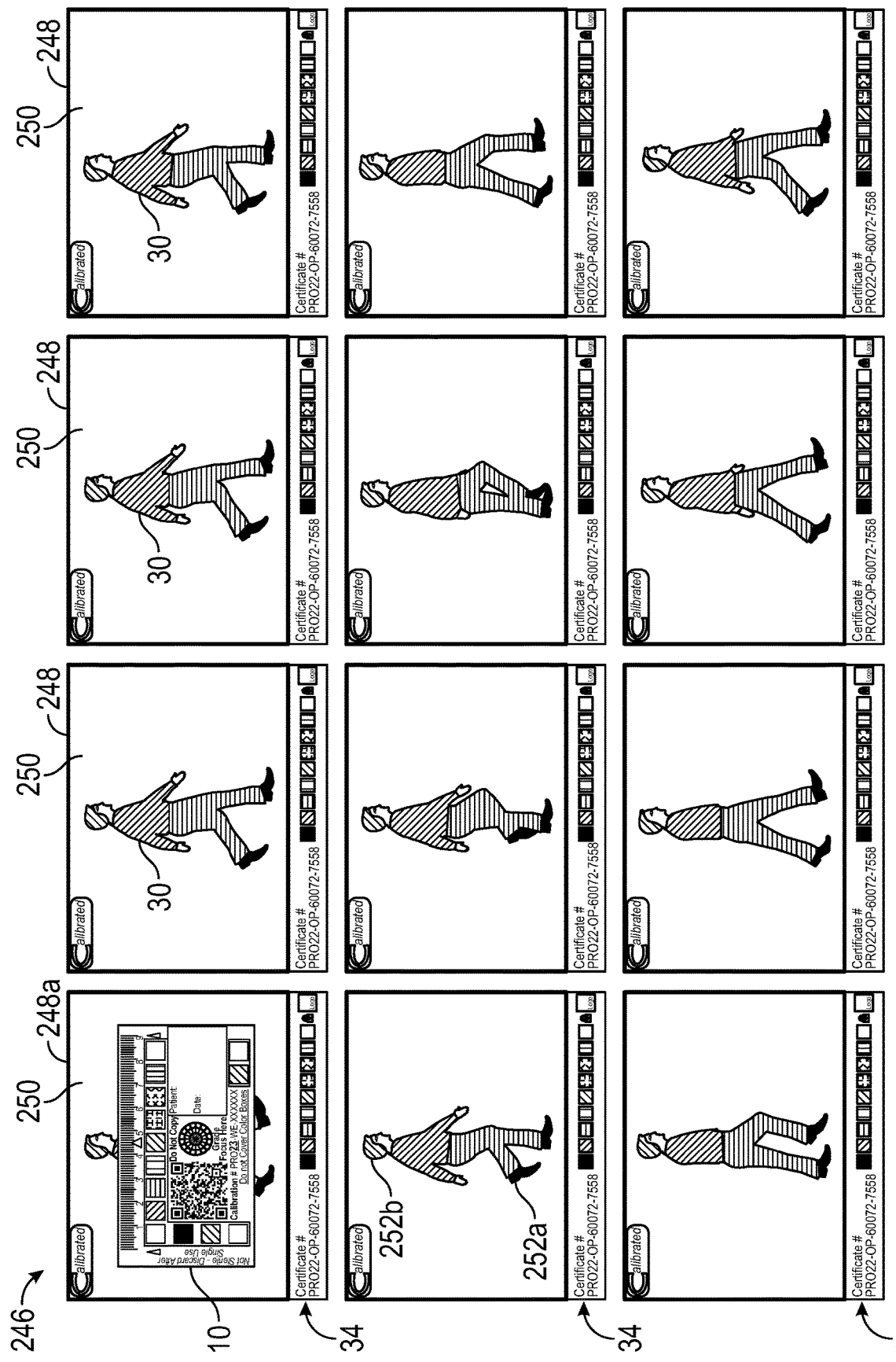
FIG. 24 shows a calibrated sequence of frames of a video with each frame having the same certification number in accordance with the present disclosure.
Figure 24A:
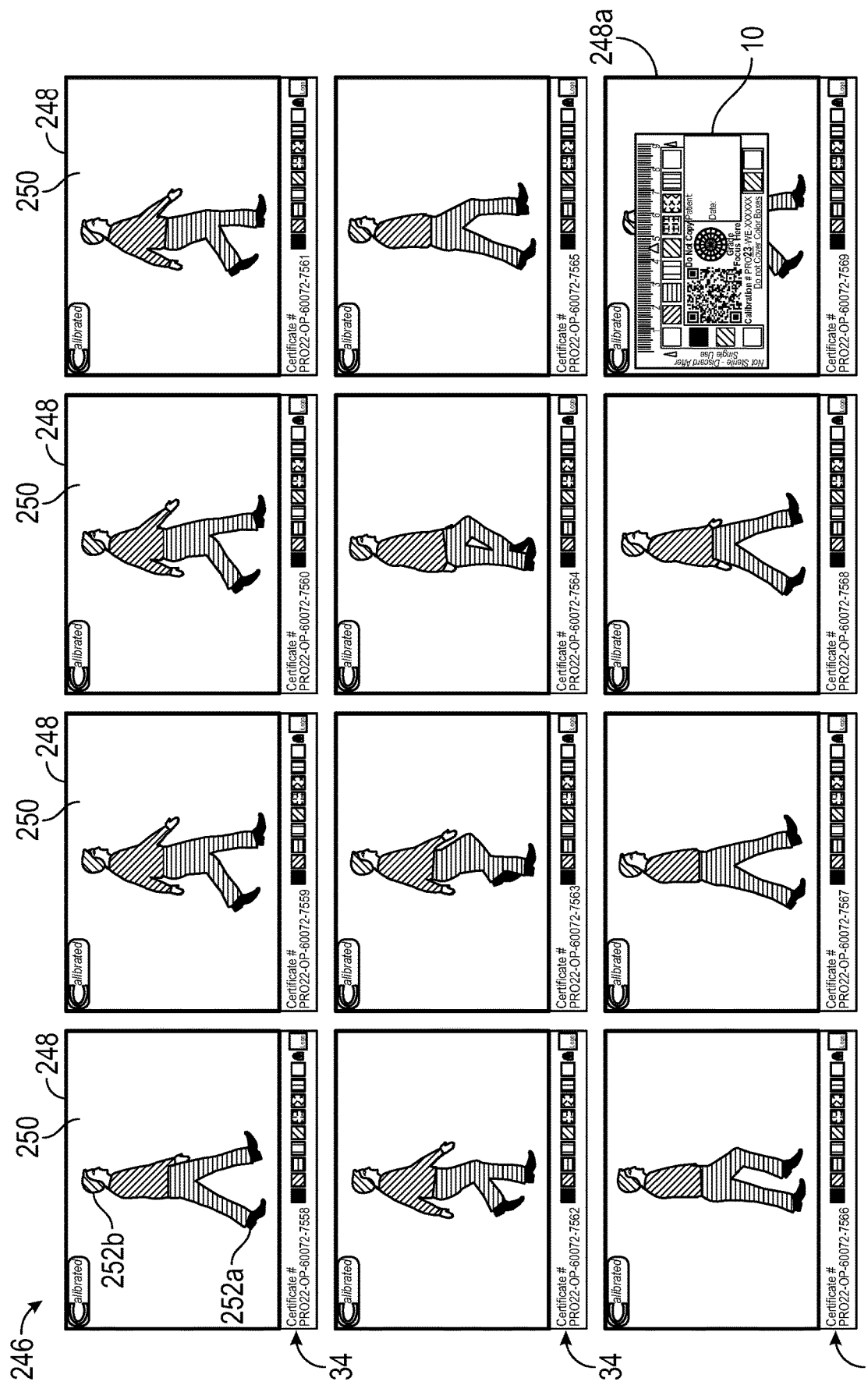
FIG. 24A shows a calibrated sequence of frames of a video with each frame having a unique certification number in accordance with the present disclosure.
Figure 24B:
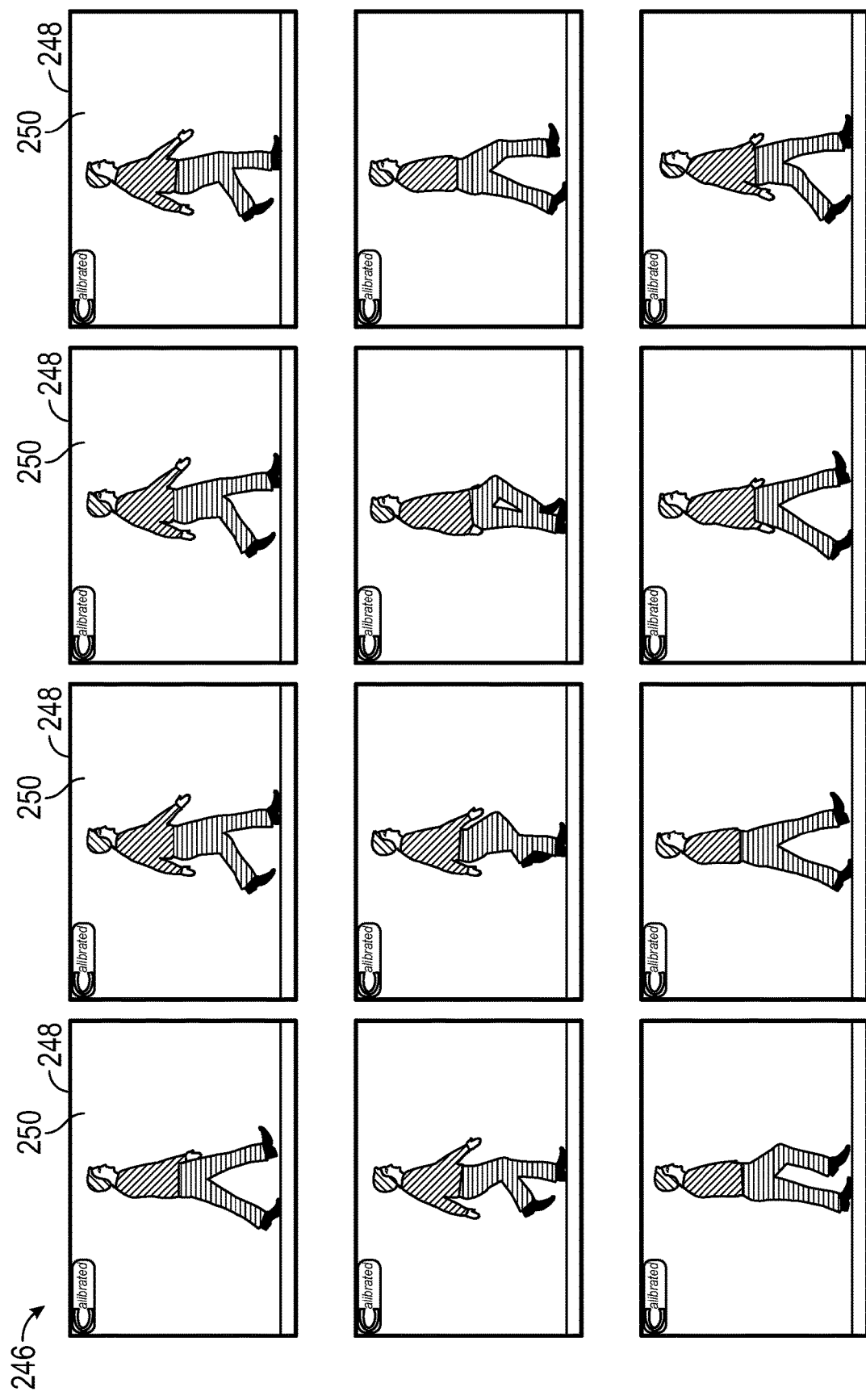
FIG. 24B shows a calibrated sequence of frames of a video without certification numbers in accordance with the present disclosure.

FIG. 24 illustrates a sequence 246 of frames 248 that have been captured and calibrated to produce the color calibrated video 244 as shown in FIG. 23. The number of frames 248 shown in FIG. 24 is shown for the purpose of illustrating the present method and showing the subject 30 in motion. Typically, a video would be captured at a frame rate of at least 24 frames per second and would thus include more frames 248 than shown in the present figures. Each frame 248 comprises a still image 250 showing the subject 30. Each frame 248 may also optionally include its own watermark 40 and certification panel 34 with a certificate number. In one embodiment, as shown in FIG. 24, each frame 248 has the same certification number so that the calibrated video 244 has a single certification number that applies to the entire video. In another embodiment, as shown in FIG. 24A, each frame 248 may have a different certification number so that each individual frame 248 may be separately certified for individual use. In another embodiment, as shown in FIG. 24B, the certification panel 34 may optionally not be displayed in each of the frames 248.

Figure 22B:
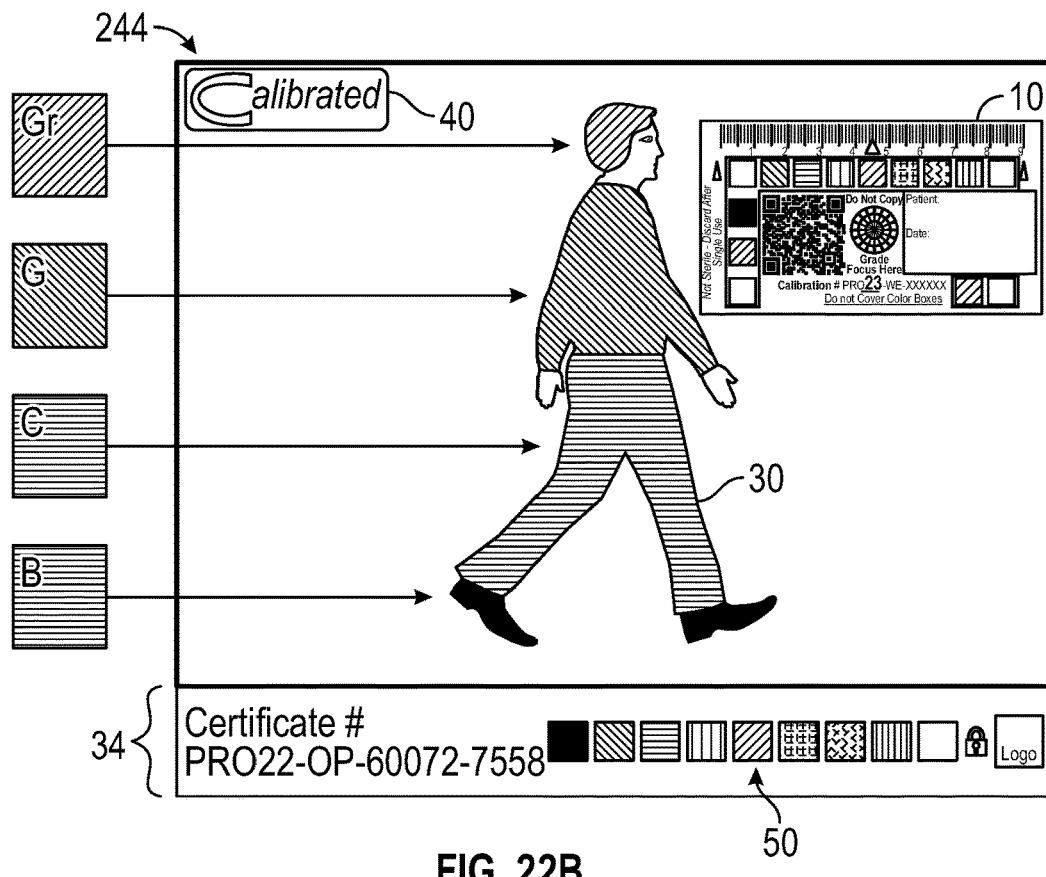
FIG. 22B shows a calibrated frame of a video with color segmentation in accordance with the present disclosure.
Figure 22C:
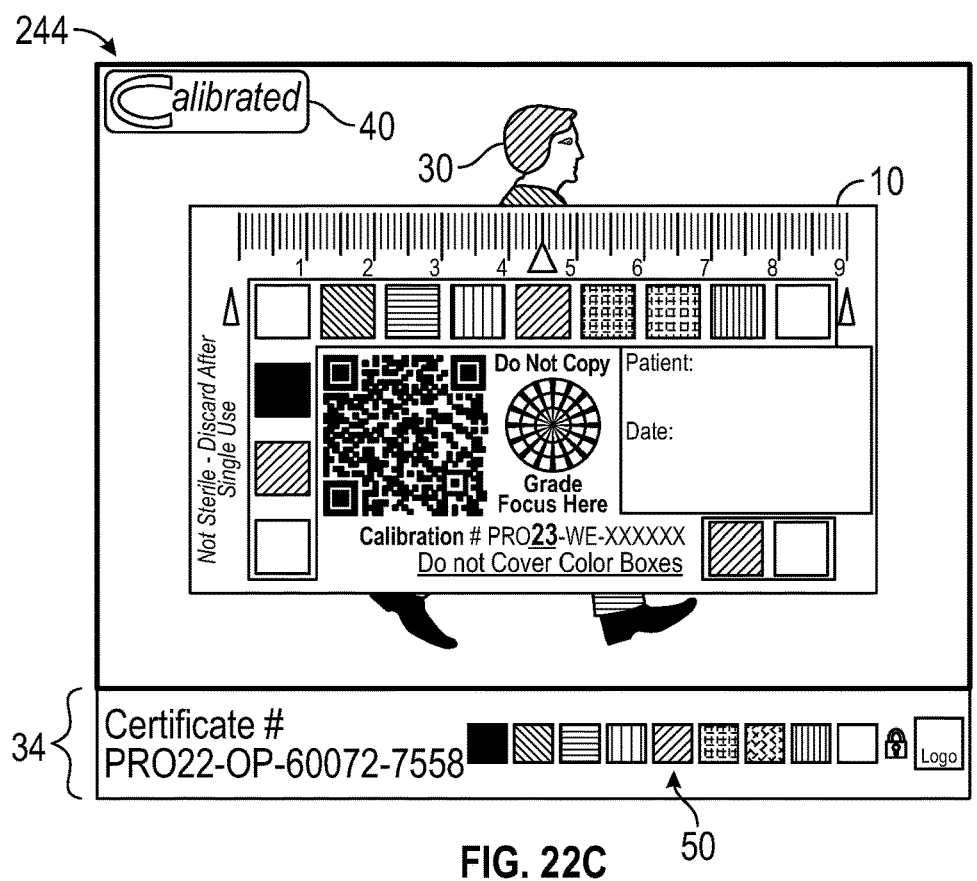
FIG. 22C shows a frame of a video with a calibration appearing in the frame for color calibration and segmentation in accordance with the present disclosure.

As shown in FIGS. 24 and 24A, a calibration slate 10 appears in at least one frame 248 of the video 244 to allow for color calibration of the frame 248 to produce the color calibrated video 244. FIG. 24 illustrates the calibration slate 10 in the first frame 248 of the sequence 246, while FIG. 24A illustrates the calibration slate 10 in the last frame 248 of the sequence 246. The calibration slate 10 may also appear in one or more frames 248 in a middle portion of the video 244. To use the calibration slate 10 for color calibration, the slate 10 should preferably be clearly and prominently displayed within the frame 248 in which the slate 10 appears so that the system 100 may effectively measure color values from the colors on the color chart 16 of the slate 10 appearing in the frame 248. FIG. 22C shows a preferable slate 10 placement in which the slate 10 is placed near the recording device 104 so that the slate 10 is prominently displayed, though the slate 10 placement as shown in FIG. 22B is also acceptable for calibration. Once a representation of the slate 10 is captured appearing in one or more frames 248, the rest of the captured video 242 may be captured without the slate 10 appearing in all of the other frames 248. For instance, FIG. 24B shows a calibrated sequence 246 of frames 248 without a calibration slate 10 appearing in any of the frames. Thus, a user 102 that is capturing a video 242 may begin the video with a calibration slate 10 appearing in the video and then continue recording the rest of the video without the need of showing the calibration slate throughout the entire video. For instance, when capturing a video 242 of a subject 30 walking or performing some other motion, the user 102 can film the calibration slate 10 with the subject 30 at some point in the video but otherwise focus on filming the movements of the subject rather than the calibration slate.

In one embodiment, the calibration factor that is calculated by comparing color values measured from the calibration slate 10 appearing in the still image 250 to known color values associated with the color chart 16 of the slate 10 may then be applied to captured colors of all of the frames 248 in a sequence 246 to color calibrate the video 244. In another embodiment, the present method may include a dynamic calibration method in which a calibration slate 10 is used to color calibrate one or more frames 248 in which the slate 10 appears and then the one or more color calibrated frames 248 are used instead of the calibration slate 10 to color calibrate additional frames 248 of a sequence 246. In this embodiment, a calibration slate 10 appears in a still image 250 of a first frame 248a of the sequence 246 of frames of a captured video 242. The first frame 248a of the sequence that is calibrated may be at any position within the sequence, such as at the beginning of the sequence, as shown in FIG. 24, or at the end of the sequence, as shown in FIG. 24A. The first frame 248a is calibrated using the calibration slate 10 in accordance with the present calibration method as previously described.

After color calibrating the first frame 248a using the calibration slate 10, the system 100 identifies a first discrete image unit that appears in the color calibrated first frame 248a. The identified discrete image unit includes at least one calibrated color since the first frame 248a has been color calibrated. Next, the system 100 identifies a second discrete image unit that appears in a second frame 248 of the sequence 246. The second frame 248 may be any single frame or multiple frames in the sequence and may include all of the frames 248 other than the first frame 248a. The first image unit of the first frame 248a and the second image unit of the second frame 248 represent the same object 252 that appears in both the first frame 248a and the second frame 248. The discrete image unit may comprise one or more pixels or other delineations of an area of a still image 250 of a frame 248 that forms at least a portion of an object 252. For instance, as shown in FIGS. 24 and 24A, the object 252 used for calibration may be the shoes 252a of a subject 30 or the hair 252b of the subject 30. Alternatively, any other object 252 captured in a frame of the video may be utilized for dynamic calibration once the colors of the object 252 have been calibrated. For instance, a portion of a wound 32 that has been color calibrated may also be utilized as an object 252 for dynamic calibration. In other embodiments, the object 252 used for calibration may be any other physical object that appears in more than one frame of the video.

The system 100 identifies the same object in both the first frame 248a and the second frame 248, e.g., shoes 252a or hair 252b, so that the colors of the object 252 in the color calibrated first frame 248a may be compared to the colors of the same object 252 in the not-yet-calibrated second frame 248. To this end, the system 100 measures a numeric color value of a calibrated color of the first image unit, which represents the color calibrated object 252 appearing in the first frame 248a after calibration, and then measures a numeric color value of a captured color of the second image unit, which represents the same object 252 appearing in the second frame 248 before calibration. For instance, a numeric color value may be measured from the portion of the first frame 248a that shows the subject's color calibrated hair 252b, and then a numeric color value may be measured from the portion of the second frame 248 that also shows the subject's hair 252b, which has not yet been color calibrated. The numeric color values of the first and second image units are then compared to each other, and then the system 100 calculates a variance between the measured numeric color value of the calibrated color of the first image unit and the measured numeric color value of the captured color of the second image unit. The system 100 then calculates a calibration factor based on the variance between the color values of the two image units. The system 100 may then color calibrate the still image 250 of the second frame 248 by adjusting one or more captured colors of the still image 250 of the second frame 248 to produce a color calibrated second frame 248. The one or more captured colors of the still image 250 of the second frame 248 are adjusted by applying the calibration factor to a numeric color value measured from the still image 250 of the second frame 248 of the sequence 246 of frames. The calibration factor may then be applied to numeric color values measured from the still image 250 of additional frames 248 of the sequence 246 of frames to produce a color calibrated video 244.

The present dynamic calibration method may be performed multiple times using multiple different individual frames to calibrate additional frames in order to calibrate an entire video. Dynamic calibration may optionally be utilized to provide color calibration in cases in which, for example, the lighting of the subject and/or environment changes during the time of capturing a video, or in which the lighting is different in different portions of a frame of the video, such as one portion being cast in a shadow, in which case a color standard for calibration may be reevaluated one or more times using different frames during the calibration process instead of being evaluated only once and then applied to frames throughout the video. Thus, in the present dynamic calibration process, a video may be calibrated at multiple points within the video using frames throughout the sequence of frames. In one embodiment, multiple calibration factors may be calculated at different points of the video based on different sets of frames throughout the video, and an extrapolation process may be used to determine additional calibration factors for additional frames located sequentially between the frames used for calculating each of the calibration factors. In addition, frames located at intervals within the video may be calibrated at those intervals based on newly calculated calibration factors to adjust for lighting condition changes, thereby dynamically adjusting the calibration for those frames relative to other frames, which are calibrated based on a different calibration factor.

Dynamic calibration of a video may be utilized to account for changes in lighting conditions that may occur during the recording of a video. For example, a subject may be recorded on a video that is recorded outdoors and begins during cloudy conditions, and then during the video the sun comes out, thereby changing the color values of the colors of objects that are captured in the video. In this example, the lighting is now brighter, but also the quality of the light changes. In this case, the light may now be "harder" with more distinct shadows due to the sunlight rather than "softer" with less defined shadows under cloudy conditions. In addition, the color of the light also changes, as direct light is typically warmer than diffused light, such as light diffused by cloud cover. Under these circumstances, a calibration factor calculated using color values measured from a calibration slate appearing in a frame captured during cloudy conditions may not provide the most accurate color calibration for frames later in the sequence of frames that are captured under conditions of increased sunlight. In this case, different frames may be calibrated independently utilizing calibration slates that appear in the different frames, such as frames captured in sunny and in cloudy conditions, even if the same subject and the same calibration slate appears in the different frames with different lighting conditions. Alternatively, objects appearing in a frame that have already been color calibrated may be utilized for dynamically color calibrating additional frames.

In another embodiment, dynamic calibration may be utilized for tracking objects 252 that appear in multiple frames and that have known color values in order to detect changes and patterns to those changes, which may be utilized to determine when different calibration factors should be calculated for calibrating different frames that show the same object under different lighting conditions. In this embodiment, objects 252 shown in multiple frames 248 may be tracked from frame to frame and then used to adjust calibration factors as needed. An object 252 appearing in a frame 248 may first be color calibrated using a calibration slate 10 as previously described. Once the object 252 has been color calibrated, the calibrated color of the object 252 as it appears in the frame 248 may then be used as a standard to track variance from that standard as the object 252 appears in subsequent frames, which may be captured under different lighting conditions. Thus, once a standard for color calibration of an object 252 is established, any changes to that object 252 can be determined, tracked, and analyzed against that standard in any other frame 248 of the sequence. As an object 252 changes within the sequence of frames, the object 252 may be color calibrated based on the calibrated color of the standard established for that object 252.

In another embodiment, objects 252 that are tracked between frames 248 may be particular objects of interest that are relevant to the subject of the video, such as a patient wound 32. Alternatively, objects 252 that are tracked between frames 248 may be "indicator" objects that are selected because these indicator objects accurately indicate changes in lighting and environment of the captured video frames. For example, the brightest and darkest objects in a frame may be utilized as indicator objects. Examples of bright objects may include light sources, such as lamps, windows, and sky, as well as objects that are naturally light-colored. Examples of dark objects may include shadows and recessed or obscured objects, as well as objects that are naturally dark-colored. As these indicator objects are tracked between frames of a sequence, changes in the indicator objects may provide leading indicators of environmental changes that could effect objects that are relevant to the subject and thus of greater relevance to the user. Calibrated color standards may be established for any object 252 appearing in a frame 248, including indicator objects. Thus, both indicator objects and "subject" objects may be tracked against the established standard for each object, which allows various qualities and attributes of each object 252 to be tracked between frames 248. Such qualities and attributes of objects 252 that may be tracked may include, but are not limited to, color intensity (concentration or saturation of the color), color value (brightness or darkness of the color), and hue (the attribute of a visible light due to which it is differentiated from or similar to primary colors). Thus, an array of qualities of an array of objects 252 may be tracked, which may establish a relative set of patterns and relationships between the objects 252. By tracking an array of qualities in an array of objects 252 in comparison to the established standard (or "calibrated state") for each object, a definable or non-relative set of patterns and relationships can be determined. Furthermore, a relative set of patterns and relationships can be compared to a non-relative set of patterns and relationships to determine a corresponding set of patterns and relationships between them. Thus, in combination, the corresponding set of patterns and relationships may be used to determine, predict, and monitor variance from the calibrated state of objects 252 in frames 248 where calibration is not possible utilizing a calibration slate 10 in the frame 248, or by utilizing known objects 252.

For example, one pattern may be to measure the quality (ies) and size(s) of both a "subject" object and an "indicator" object in multiple frames 248 to track changes of both objects in comparison to their calibrated states to define a non-relative set of patterns and relationships between the two objects. For instance, patterns and relationships of the changes between when the brightest objects grow in size and intensity and when the darkest objects decrease in size and intensity in the same frames 248 may be determined. In addition, a mathematical relationship between an increase of the brightest indicator object and a decrease of the darkest indicator object may be determined. In another example, a mathematical relationship between changes in quality and size of "subject" objects appearing in the same frame may be determined. Further, mathematical relationships between changes in quality and size of "subject" objects may then be compared to mathematical relationships between changes in quality and size of "indicator" objects to determine patterns and mathematical relationships between the "subject" and "indicator" objects. Thus, the present method provides a method to dynamically track objects 252 in frames 248 in order to determine when those objects require calibration back to the established standard for an object throughout the video.

In another embodiment, different areas of a single still image 250 or single frame 248 may be calibrated separately using different calibration factors. Generally, a neutral grey color (for instance, a grey having the same value of 125 in red, green, and blue) is a good candidate color for calibrating an image and may be utilized to calibrate the entire image by adjusting the RBG values of all captured colors according to the variance of the RGB color values of the grey color as measured in the captured image and compared to the known RBG values of 125. Once calibrated, the colors of the color chart 16 appearing in the image (which have thus been color calibrated) may then be subjectively compared to the colors in the color chart of the actual calibration slate 10 to make an immediate assessment of the overall accuracy of the calibration of the entire image. In addition, the color values of the color calibrated white 16b chip on the slate appearing in the image may be measured after calibration and compared to the known color values of the white 16b chip as a check on the accuracy of the calibration. If these values are within a desired tolerance, the image may be determined to be calibrated.

In some embodiments, different colors from the color chart 16 of the calibration slate 10 may be utilized to calculate different calibration factors, which may then be applied to color values of colors appearing in different portions of the image. This method may result in an overall image with greater color accuracy than using the same calibration factor(s) applied to the entire image. For instance, in the case of a wound 32, a portion of the wound that is predominantly red in color may be calibrated using a calibration factor calculated based on the variance of color values from the values measured from the red 16i chip of the calibration slate. Other portions of the wound appearing in the image may then be calibrated using a different calibration factor calculated based on the color of the color chart that is generally closer in color to that portion of the wound. In another example, portions of an image that are shaded may be calibrated based on colors appearing on a slate in the shaded portion of the image, and other portions of the image that are not shaded may be calibrated based on colors appearing on the slate outside of the shaded portion of the image. For instance, a calibration slate 10 may have more than one grey 16c chip. If one grey chip is shaded and another grey chip is not shaded, the shaded chip may be utilized for calibrating shaded portions of the image and the chip that is not shaded may be utilized for calibrating portions of the image that are not shaded, which may provide a more accurate calibration of the entire image overall.

Figure 25A:
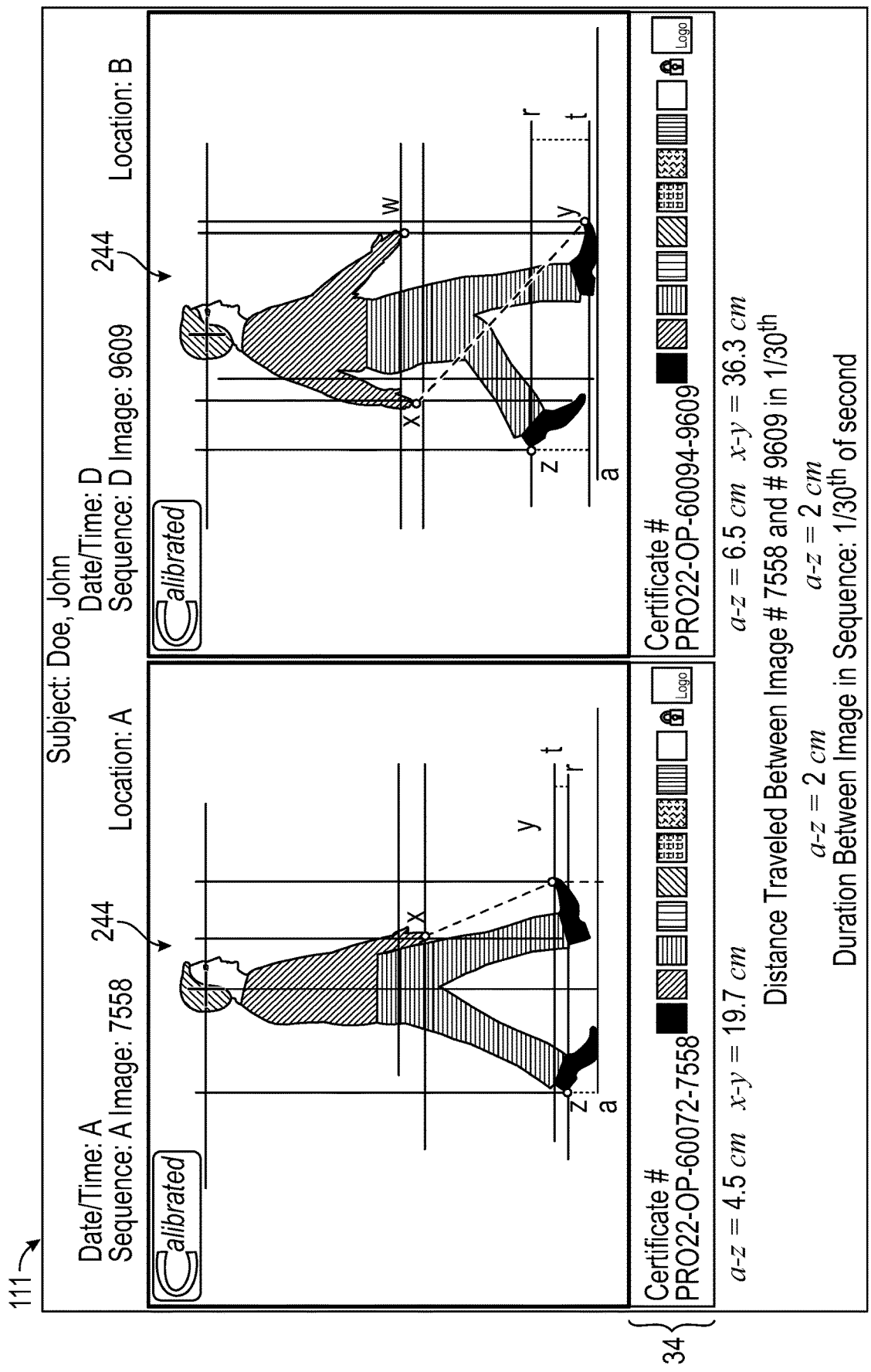
FIG. 25A shows a graphical user interface showing two calibrated frames of a video out of sequence with distance measurements in accordance with the present disclosure.

The system 100 may also be utilized to determine distance measurements between objects relating to the subject 30 and appearing in the still image 250 of one or more frames 248 based on known measurements of one or more objects printed on the calibration slate 10 appearing in the still image 250, such as the QR code 14, the focus chart 18, or some other feature printed on the slate, or combinations thereof, by comparing the known measurements of objects on the slate 10 with measurements obtained from the image 250 that includes the calibration slate 10 appearing in the image 250. As used herein, the term "objects" may refer to any spatial points appearing in the image with the subject 30, which may include portions of the patient subject 30 or any other points displayed in the image of the subject. For instance, as shown in FIGS. 25 and 25A, the system 100 may be utilized to measure distances between body parts of the subject for the purpose of analyzing the subject's movement and evaluating the subject based on the movements. For instance, as shown in FIG. 25, the system 100 may identify a point at the fingertips of the subject's right hand (x) in multiple frames 248 and also identify a point at the tips of the subject's shoes on the subject's right foot (y). The system 100 may then calculate the distance between these points in different frames 248 of the calibrated video 244 to evaluate the subject's movements. Similarly, the system 100 may identify a point at the bottom of the back of the subject's left heel (z) and a point at the level of the floor (a) on which the subject is walking. The system 100 may then calculate the distance between these points in different frames 248 to evaluate the subject's walking motion. These measurements may be determined between any two frames 248 of a sequence 246 of frames. FIG. 25 illustrates measurements taken on sequential frames 248 captured as part of the same sequence (A) of a video. FIG. 25A illustrates measurements relating to a subject captured within frames 248 captured as part of two separate sequences (Sequence "A" and Sequence "D") of separate videos recorded at different dates and times, which may allow for analysis of how a subject's movements change over a period of time. The analysis of these measurements may include pattern recognition and prediction using various methods including, but not limited to, mathematical models and artificial learning and self-learning systems and methods. Such measurements of objects and measurements between objects may be determined, compared, and analyzed in videos, as well as in still images and three-dimensional models.

In one embodiment, the present system 100 may be utilized to extract particular frames 248 from a sequence 246 that incorporate high-level semantic information corresponding to key-events, or "keyframes," from a video 244. After extracting keyframes 248 from a video sequence, an overall context of a video 244 may be established by the keyframes as a collection of representations taken from individual frames of the video. These representations may refer either to the actual keyframes or to robust feature descriptors extracted from the keyframes. The former leads to applications related to video summarization and browsing, where instead of the entire video 244 the user may visualize a number of preselected keyframes 248. Extracting descriptors from keyframes is generally related to video indexing and image retrieval, where the goal is to retrieve keyframes similar to a query frame. Because there are generally many redundancies among the frames 248 of a sequence 246, the goal of selecting particular keyframes is to select those frames that contain as much salient information as possible relating to the subject. Indicative image features may include features such as color, texture, edges, MPEG-7 motion descriptors, and optical flow. Among the various approaches employed, sequential comparison-based methods compare frames subsequent to a previously extracted keyframe, whereas global-based methods perform global frame comparison by minimizing an objective function. Reference-based methods generate a reference frame and then extract keyframes based on the comparison of the shot frames with the reference frame. Other methods of selecting keyframes may include keyframe selection based on frame clustering and trajectory curve representation of the frame sequence. Individual frames of a sequence may be identified for various criteria of interest manually or by employing various methods such as those described above to produce means of indexing, summarizing, comparing, and measuring objects within frames and between frames in order to analyze, deduce outcomes and patterns, and also for predictions based on a body of keyframes. In one example, individual frames 248 shown in FIG. 25 may be selected as keyframes, and an analysis may be performed across a single video 244 or three-dimensional video. In another example, the frames 248 shown in FIG. 25A may be selected as keyframes, and a similar analysis may be performed across different sequences 246, videos 244, or three-dimensional videos.

Figure 15:
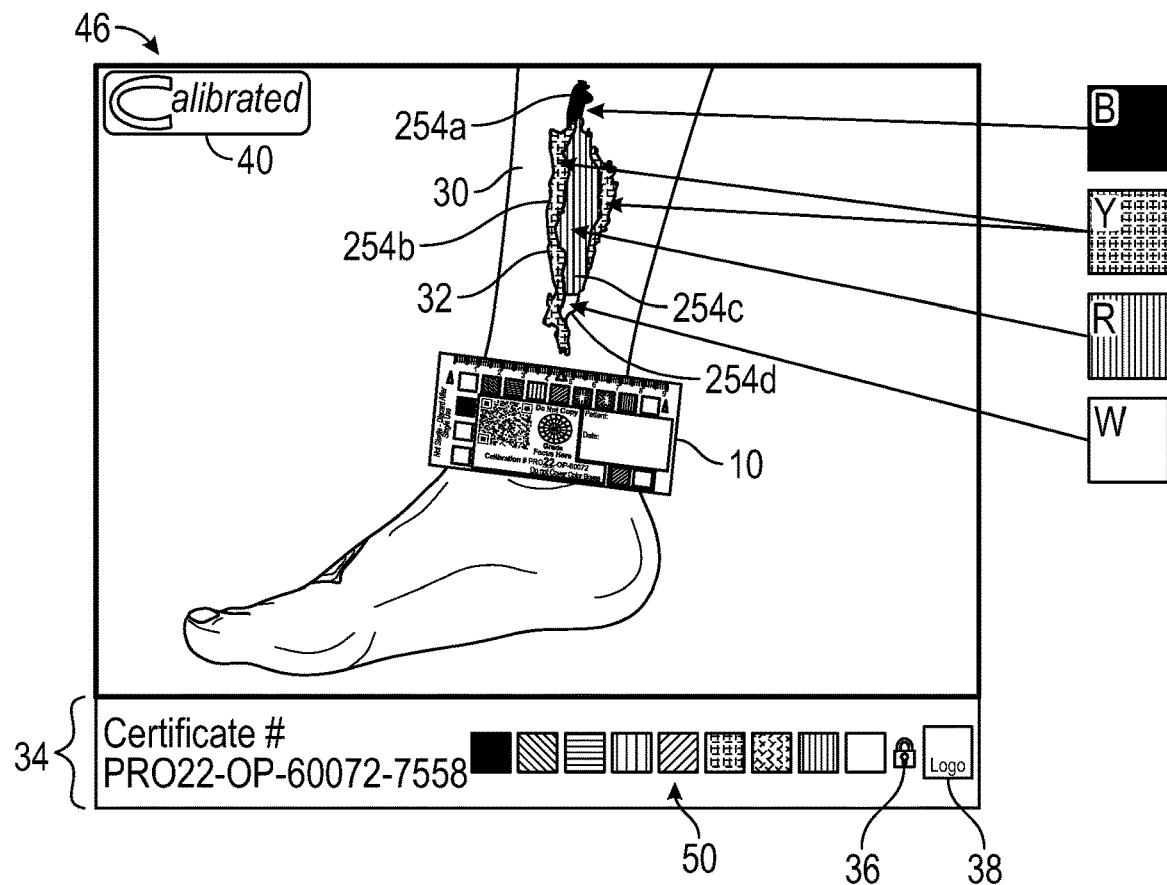
FIG. 15 shows a calibrated image with color segmentation in accordance with the present disclosure.
Figure 16:
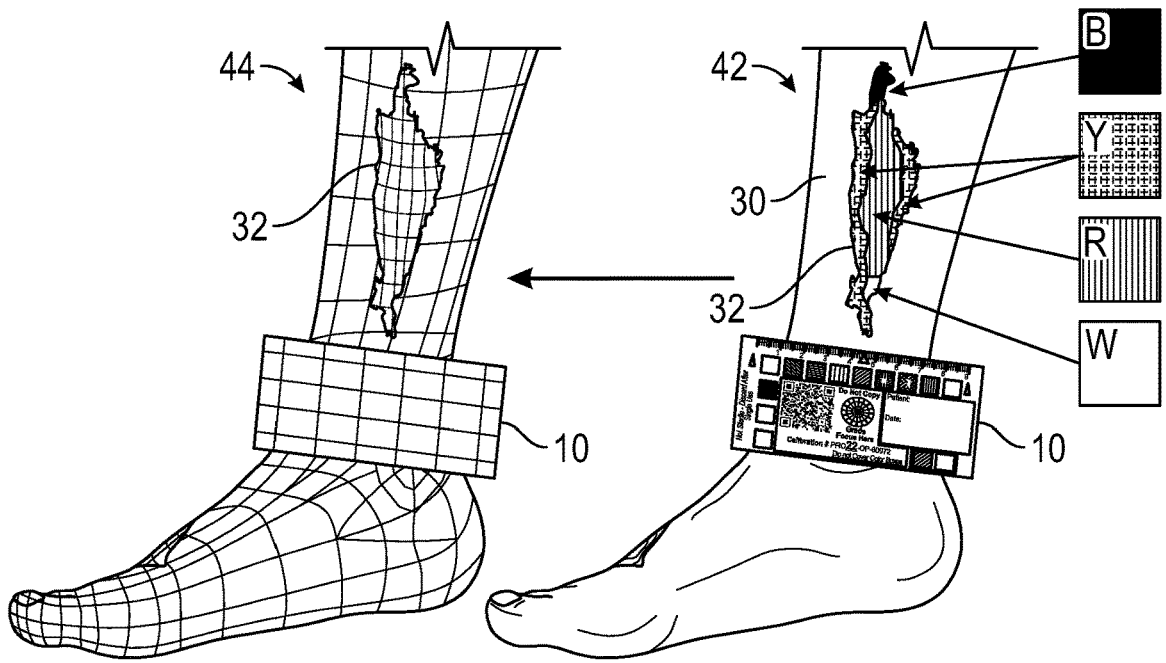
FIG. 16 shows a three-dimensional model of a two-dimensional image of a subject with color segmentation in accordance with the present disclosure.
Figure 17:
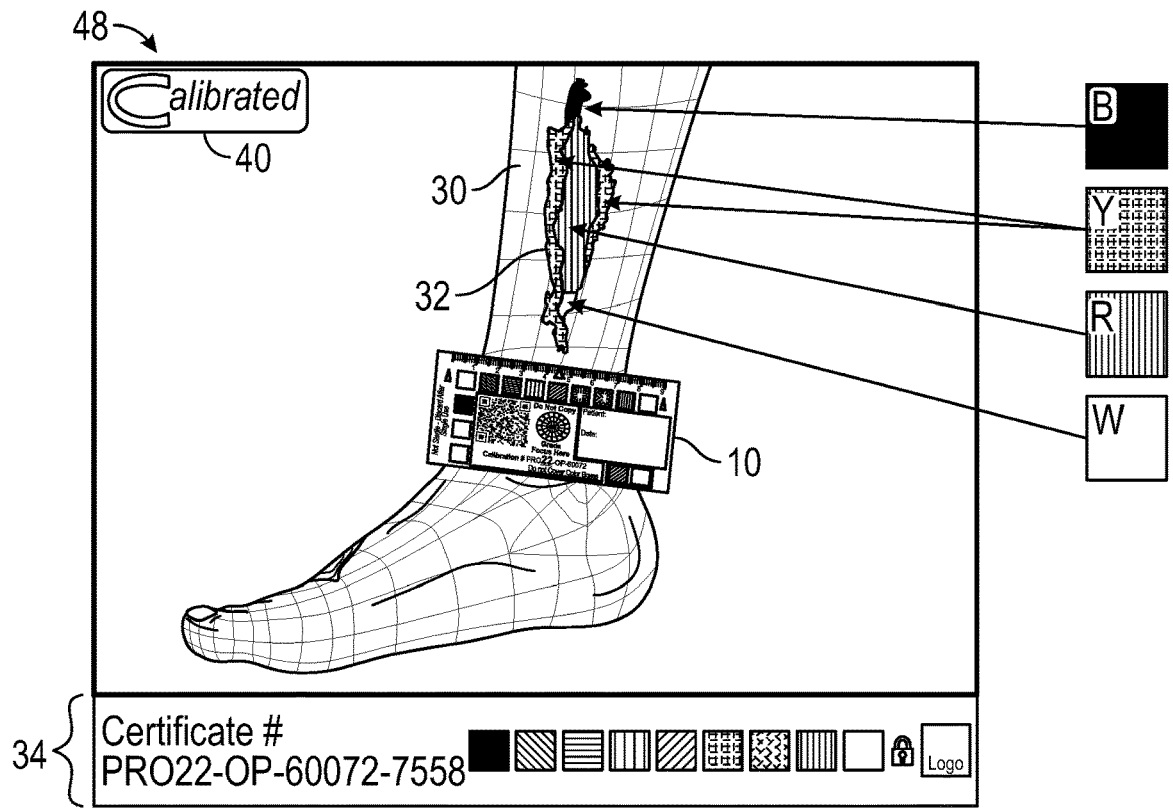
FIG. 17 shows a calibrated three-dimensional image with color segmentation in accordance with the present disclosure.
Figure 18:
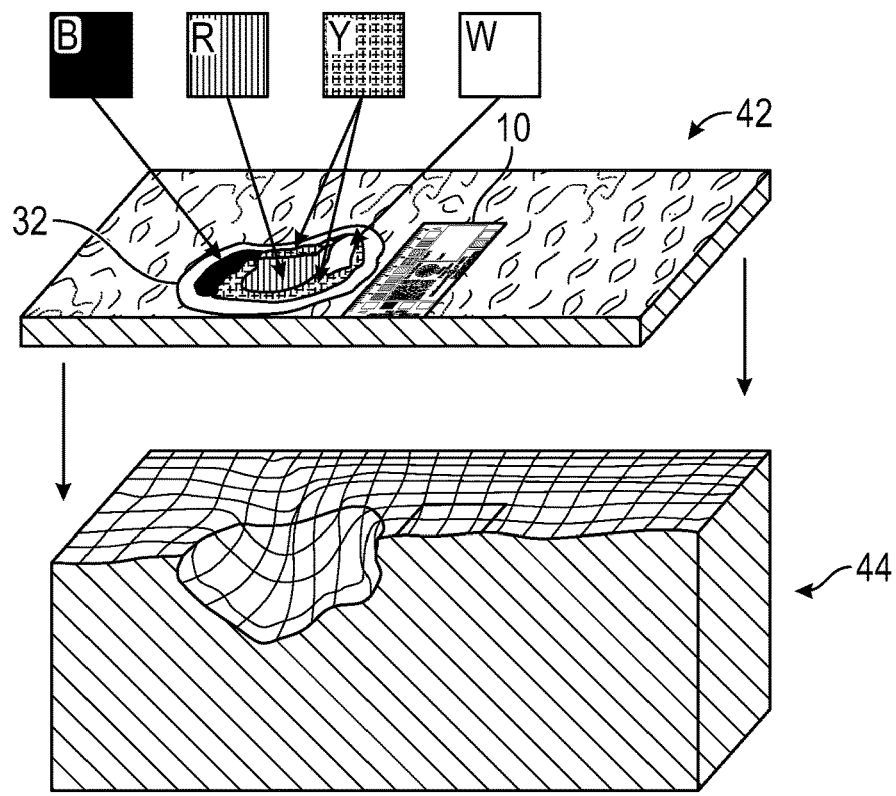
FIG. 18 shows a three-dimensional model of a two-dimensional image of a subject with color segmentation in accordance with the present disclosure.
Figure 19:
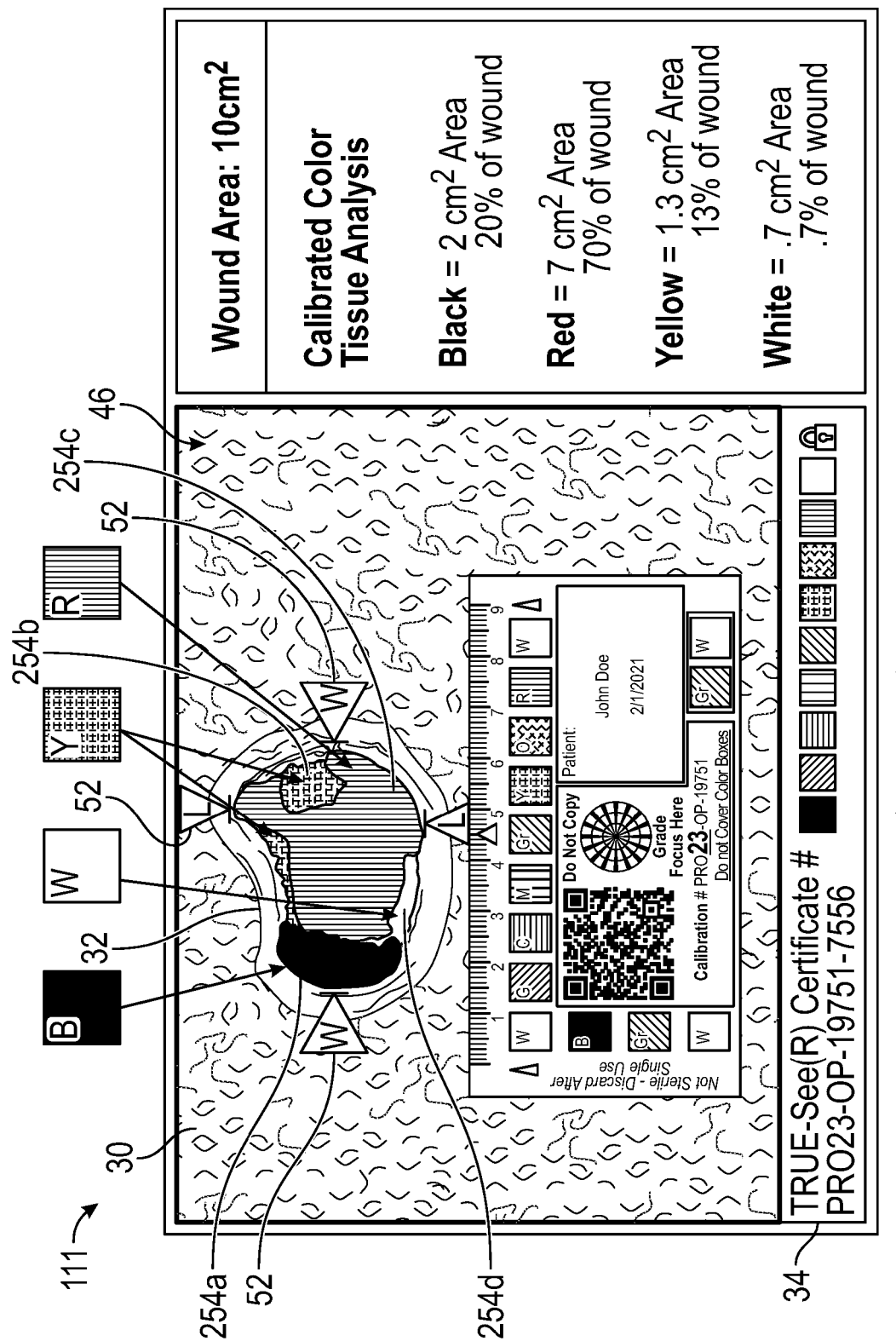
FIG. 19 shows a graphical user interface showing a calibrated image with color segmentation in accordance with the present disclosure.
Figure 20:
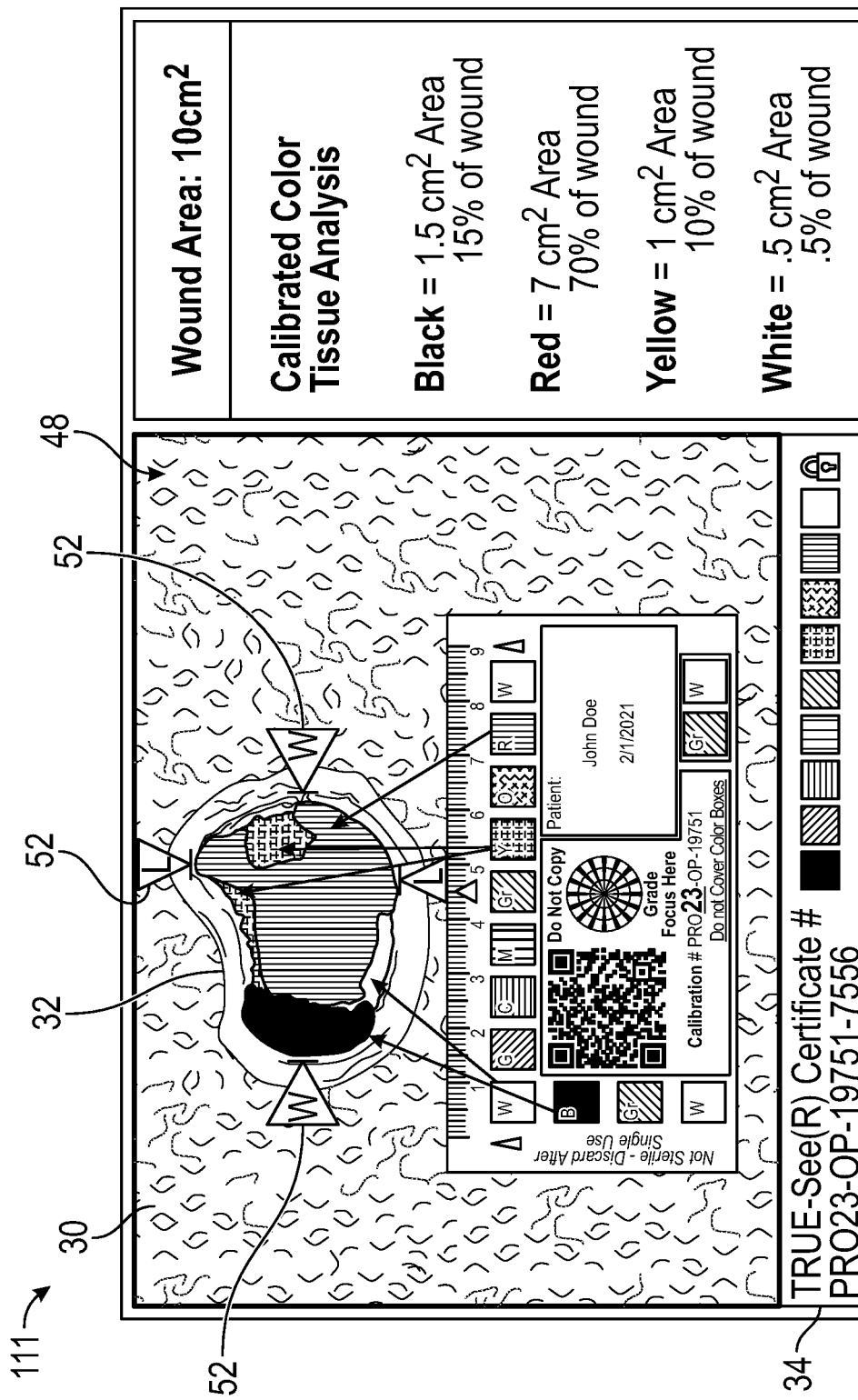
FIG. 20 shows a graphical user interface showing a calibrated image with color segmentation in accordance with the present disclosure.
Figure 21:
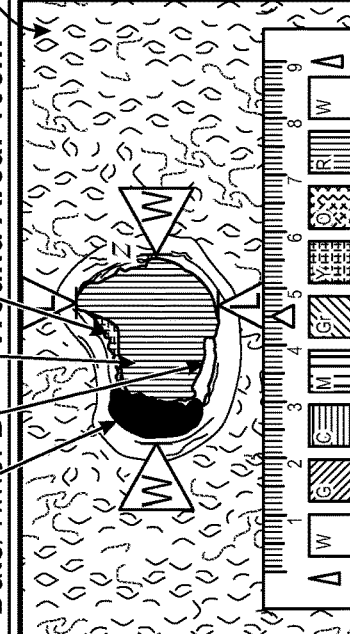
FIG. 21 shows a graphical user interface showing multiple calibrated images with color segmentation illustrating changes in a patient wound over a period of time in accordance with the present disclosure.

In another aspect, a method of segmenting and mapping colors of images 46 or videos 244 is provided. The method may be applied to images 46 or videos 244 that are two-dimensional 46 or three-dimensional 48, including individual still images 250 of video frames 248 or three-dimensional models 44. In the context of color segmenting and mapping, an "image" may include a still image from a frame of a video. The method comprises first color calibrating an image 42 or video 242 utilizing a calibration slate 10 appearing in the still image 42, 250 or at least one frame 248 of the video 242. FIG. 15 shows a color calibrated two-dimensional image 46 to which the present color segmenting and mapping method has been applied, and FIG. 17 shows a color calibrated three-dimensional image 48 to which the present color segmenting and mapping method has been applied after constructing a three-dimensional model 44 of the image as shown in FIG. 16. FIG. 18 shows an additional example of the method being applied to a three-dimensional model 44. FIGS. 19 and 20 show two-dimensional and three-dimensional color segmentation and mapping, respectively, of the wound 32 shown in FIG. 18. FIG. 21 shows a graphical user interface 111 that may be utilized for viewing, mapping, and analyzing color calibrated images 46. As shown in FIG. 21, multiple calibrated and mapped images may be shown within a single interface so that the images may be compared to analyze how a wound has changed with time.

Once the image or video has been color calibrated in accordance with the present calibration method, a target color having a known numeric color value may be selected by a user of the system 100. One or more target colors may be selected based on the particular application. For instance, when calibrating an image of a wound 32, a red, yellow, black, and/or white target color may be selected as these colors are often present in wounds and represent different types of tissues commonly observed in wounds. FIGS. 15 and 19 show areas 254 of these four target colors being mapped on a wound 32. Each target color has a known numeric color value associated with the target color. Next, the user selects a color value tolerance relating to the known numeric color value associated with the target color. For instance, a desired tolerance of 10% from a selected red target color having known numeric color values may be selected. The desired tolerance may be selected based on the particular application and selected target color. Any target color having any known numeric color values may be selected, and any tolerance level may be selected for use with the present method. The system 100 then measures a numeric color value from one or more calibrated colors of the color calibrated image 46 or video 244 and compares the measured numeric color value to the known numeric color value associated with the target color to determine whether the measured numeric color value is within the selected color value tolerance of the known numeric color value. The system 100 then maps an area 254 of the color calibrated image 46 or video 244 in which one or more calibrated colors are within the selected color value tolerance of the known numeric color value associated with the selected target color. The measured color values may be measured from discrete image units, such as one or more pixels, of the color calibrated image. The discrete image units may be located within any portion of an image or throughout the entire image. The locations of one or more image units may be selected by the user for the purpose of mapping the colors of only a particular portion of the image having significance to the user, such as a wound 32. Thus, only a portion of the image may be mapped to delineate colors in that portion rather than the entire image being mapped. Color values measured from the calibrated colors of the image may be measured from a plurality of discrete image units of the color calibrated image so that each image unit is small enough to produce mapped areas having a desired level of color detail. To this end, each image unit may comprise only a single pixel or similarly sized unit of area.

The image units that are within the color value tolerance of the target color may be delineated from other areas having colors that are not within the tolerance to produce a mapped area that is visually displayed on the color calibrated image 46. Multiple target colors may be selected to segment multiple colors from each other and produce mapped areas of different colors displayed on the image. For instance, FIGS. 15 and 19 show wounds 32 having four mapped colors, which, in this case, are black, yellow, red, and white. To map the colors, the system 100 may group together image units of a plurality of image units that are within the selected color value tolerance and then visually delineate the area that includes the grouped image units on the color calibrated image 46. Color areas may be visually delineated in any suitable manner, such as by visually displaying a line that surrounds a mapped area of a particular color. In a preferred embodiment, as best seen in FIGS. 15 and 19, areas may be mapped by visually filling in an area with the selected target color for which the colors in that area are within the tolerance. For instance, one area 254*a* of a wound 32 has been mapped with a black color, which indicates that the calibrated colors of the color calibrated image in each discrete image unit within that area 254*a* were all within the selected color value tolerance for the black target color. Similarly, another area 254*b* has been mapped with a yellow color, which indicates that the calibrated colors of the color calibrated image in each discrete image unit within that area 254*a* were all within the selected color value tolerance for the yellow target color. Likewise, area 254*c* has been mapped with a red target color, and area 254*d* has been mapped with a white target color. This allows a user to visually evaluate the condition of a wound quickly by analyzing the general colorations of the wound and relative size of each color area 254.

In a preferred embodiment, the color calibrated image 46, 48 is an image related to the medical field, and the target colors are selected based on tissue color of tissue appearing in the color calibrated image, such as a wound 32 in which the tissue color is a wound color of wound tissue. However, the present color mapping method may also be utilized in other types of applications not related to the medical field, including video applications. FIG. 24 illustrates the present color mapping method being applied to frames 248 of a color calibrated video 244. To illustrate the method, four different areas of different colors have been delineated and mapped in each frame 248 of the video 244. These four areas include areas of the color of the hair, shirt, pants, and shoes of the subject 30. These four areas have been mapped on each still image 250 of each frame 248 by filling in each of the four areas with the selected target color. For instance, if the subject's hair is brown, the user may select a target color of brown to delineate and map that area of the frame 248. Similarly, if the subject has black shoes, a target color of black may be selected to map the area of the frame 248 in which the shoes appear. The color mapping method may also be applied to the colors of color calibrated three-dimensional images 48, as shown in FIG. 20.

The calibration slate 10 may also be utilized to determine size measurements of one or more mapped areas 254 on the calibrated image 46 based on known measurements of one or more objects printed on the calibration slate 10 that appears in the image 46, such as the QR code 14, the focus chart 18, or some other feature printed on the slate, or combinations thereof, by comparing the known measurements of objects on the slate 10 with measurements of mapped areas 254 appearing within the same image as the slate 10. Such measurements may include any measurements of the dimensions of a mapped area 254 such as a length or width of the area at any point of the area 254, a circumference of a mapped area, or any other physical dimensions of the mapped area. Based on these measurements, a geometric area of each mapped area 254 may be calculated, and a percentage of each mapped area 254 displayed on the color calibrated image may also be calculated based on a total geometric area that includes all mapped areas 254*a-d*. This allows for comparisons of the geometric area of a mapped area 254 to earlier images to determine how a mapped area has changed with time or to other mapped areas to determine how the relative relationship of different mapped areas has changed. In the case of wound analysis, this allows a medical professional to evaluate how a wound 32 changes over time by analyzing how, for instance, a red mapped area 254*c* of the wound 32 changes in size or how other mapped areas 254 of the wound also change. Thus, the present method may be utilized to evaluate the condition of a wound 32 or the healing progress by of the wound by determining how different areas 254 of the wound of different colors have changed with time.

It is understood that versions of the present disclosure may come in different forms and embodiments. Additionally, it is understood that one of skill in the art would appreciate these various forms and embodiments as falling within the scope of the invention as disclosed herein.

What is claimed is:

1. A method comprising the steps of:
   color calibrating an image, wherein the color calibrating step comprises:
      capturing an image of a subject on an image recording device, wherein the captured image includes a calibration slate appearing in the captured image, wherein the calibration slate has a print run number that identifies a batch of printed calibration slates which includes the calibration slate appearing in the captured image and a color chart comprising at least one color,
      measuring a numeric color value from the at least one color of the color chart of the calibration slate appearing in the image,
      reading the print run number,
      associating the print run number with the batch of printed calibration slates which includes the calibration slate appearing in the captured image, wherein each printed calibration slate in the batch of printed calibration slates is substantially similar, wherein the measured numeric color value from the at least one color of the color chart has a corresponding known numeric color value associated with the batch of printed calibration slates,
      comparing the measured numeric color value of the at least one color of the color chart to the corresponding known numeric color value associated with the batch of printed calibration slates,
      calculating a variance between the measured numeric color value of the at least one color of the color chart and the corresponding known numeric color value associated with the batch of printed calibration slates,
      calculating a calibration factor based on the variance between the measured numeric color value of the at least one color of the color chart and the corresponding known numeric color value associated with the batch of printed calibration slates, and
      color calibrating the captured image by adjusting one or more captured colors of the captured image to produce a color calibrated image having one or more calibrated colors, wherein the one or more captured colors of the captured image are adjusted by applying the calibration factor to a numeric color value measured from the captured image;

after color calibrating the captured image, selecting a target color having a known numeric color value associated with the target color;

selecting a color value tolerance relating to the known numeric color value associated with the target color;

measuring a numeric color value of the one or more calibrated colors of the color calibrated image;

comparing the measured numeric color value of the one or more calibrated colors to the known numeric color value associated with the target color;

determining whether the measured numeric color value of the one or more calibrated colors is within the color value tolerance of the known numeric color value associated with the target color; and mapping an area of the color calibrated image in which the one or more calibrated colors are within the color value tolerance of the known numeric color value associated with the target color.

2. The method of claim 1, further comprising the steps of:

selecting a second target color having a known numeric color value associated with the second target color;

selecting a second color value tolerance relating to the known numeric color value associated with the second target color;

comparing the measured numeric color value of the one or more calibrated colors to the known numeric color value associated with the second target color;

determining whether the measured numeric color value of the one or more calibrated colors is within the second color value tolerance of the known numeric color value associated with the second target color; and mapping a second area of the color calibrated image in which the one or more calibrated colors are within the second color value tolerance of the known numeric color value associated with the second target color.

3. The method of claim 2, further comprising the step of calculating a percentage of each area of the color calibrated image based on a total area that includes each area.

4. The method of claim 1, wherein the step of measuring a numeric color value of the one or more calibrated colors of the color calibrated image comprises measuring the numeric color value of the one or more calibrated colors within a plurality of discrete image units of the color calibrated image.

5. The method of claim 4, wherein each of the image units comprises one or more pixels.

6. The method of claim 4, wherein the step of mapping an area of the color calibrated image comprises grouping image units of the plurality of image units that are within the color value tolerance and visually delineating the area that includes the grouped image units on the color calibrated image.

7. The method of claim 1, further comprising the step of determining a size measurement of the area based on known measurements of one or more objects printed on the calibration slate appearing in the image.

8. The method of claim 1, wherein the color calibrated image is an image related to the medical field, wherein the target color is selected based on a tissue color of tissue appearing in the color calibrated image.

9. The method of claim 8, further comprising the step of associating the calibration slate appearing in the captured image with a patient based on patient identification information.

10. The method of claim 1, wherein the calibration slate also has a unique identifier that individually identifies the calibration slate appearing in the image, wherein the method further comprises the steps of reading the unique identifier and validating the calibration slate based on the unique identifier.

11. The method of claim 10, wherein the unique identifier is in the form of a machine-readable bar code.

12. The method of claim 1, further comprising the step of embedding a hash code within a file containing data related to the color calibrated image, wherein the hash code is designed to change automatically if the data is altered.

13. The method of claim 12, wherein the color calibrated image includes a graphically displayed icon that visually indicates that the hash code has not changed.

14. The method of claim 1, further comprising the step of certifying the color calibrated image by embedding a unique certification number within the color calibrated image.

15. The method of claim 1, further comprising the step of graphically displaying a second color chart within the color calibrated image, wherein the second color chart comprises a set of colors having known numeric color values, wherein each color in the set of colors of the second color chart is substantially similar to a respective corresponding color associated with the batch of calibration slates.

16. The method of claim 1, wherein the calibration slate appearing in the captured image further includes a focus chart comprising concentrically arranged shapes, wherein the focus chart is configured such that it can be used for grading the focus of the captured image, wherein the method further comprises the step of focusing the captured image using the focus chart before capturing the captured image.

17. The method of claim 1, further comprising the step of displaying a watermark within the color calibrated image, wherein the watermark is configured to indicate that the color calibrated image has been color calibrated.

18. A method comprising the steps of:

color calibrating a three-dimensional image, wherein the color calibrating step comprises:

capturing a plurality of two-dimensional images of a subject on an image recording device, wherein each of the captured two-dimensional images shows the same subject appearing in each respective two-dimensional image, wherein each of the captured two-dimensional images includes a calibration slate appearing in each respective captured two-dimensional image, wherein the calibration slate appearing in each respective captured two-dimensional image is the same calibration slate, wherein the calibration slate has a print run number that identifies a batch of printed calibration slates which includes the calibration slate appearing in each of the two-dimensional images and a color chart comprising at least one color, constructing a three-dimensional image of the subject using the plurality of captured two-dimensional images, wherein the constructed three-dimensional image shows the calibration slate that appears in each respective captured two-dimensional image, measuring a numeric color value from the at least one color in the color chart of the calibration slate appearing in each respective captured two-dimensional image, reading the print run number;

associating the print run number with the batch of printed calibration slates which includes the calibration slate appearing in each respective captured two-dimensional image, wherein each calibration slate in the batch is substantially similar, wherein the measured numeric color value has a corresponding known numeric color value associated with the batch of calibration slates, comparing the measured numeric color value to the corresponding known numeric color value, calculating a variance between the measured numeric color value and the corresponding known numeric color value, calculating a calibration factor based on the variance between the measured numeric color value and the corresponding known numeric color value, and color calibrating the constructed three-dimensional image by adjusting one or more captured colors of each respective captured two-dimensional image or of the constructed three-dimensional image to produce a color calibrated three-dimensional image having one or more calibrated colors, wherein the one or more captured colors are adjusted by applying the calibration factor to numeric color values measured from each respective captured two-dimensional image or from the constructed three-dimensional image;

after color calibrating the constructed three-dimensional image, selecting a target color having a known numeric color value associated with the target color;

selecting a color value tolerance relating to the known numeric color value associated with the target color;

measuring a numeric color value of the one or more calibrated colors of the color calibrated three-dimensional image;

comparing the measured numeric color value of the one or more calibrated colors to the known numeric color value associated with the target color;

determining whether the measured numeric color value of the one or more calibrated colors is within the color value tolerance of the known numeric color value associated with the target color; and mapping an area of the color calibrated three-dimensional image in which the one or more calibrated colors are within the color value tolerance of the known numeric color value associated with the target color.

19. The method of claim 18, further comprising the step of embedding a hash code within a file containing data related to the color calibrated three-dimensional image, wherein the hash code is designed to change automatically if the data is altered.

20. The method of claim 18, further comprising the step of certifying the color calibrated three-dimensional image by embedding a unique certification number within the color calibrated three-dimensional image.

* * * * *